(12) United States Patent
Almirante et al.

(10) Patent No.: US 7,169,805 B2
(45) Date of Patent: Jan. 30, 2007

(54) CAPTOPRIL DERIVATIVES

(75) Inventors: Nicoletta Almirante, Milan (IT); Ennio Ongini, Segrate (IT); Piero Del Soldato, Monza (IT)

(73) Assignee: Nicox S.A., Sophia Antipolis (FR)

( * ) Notice: Subject to any disclaimer, the term of this patent is extended or adjusted under 35 U.S.C. 154(b) by 6 days.

(21) Appl. No.: 10/849,560

(22) Filed: May 20, 2004

(65) Prior Publication Data

US 2004/0259808 A1 Dec. 23, 2004

(30) Foreign Application Priority Data

May 28, 2003 (EP) ................................ 03101553

(51) Int. Cl.
*A61K 31/401* (2006.01)
*C07D 207/08* (2006.01)
*A61K 31/5377* (2006.01)
*A61K 31/454* (2006.01)
*C07D 401/12* (2006.01)
*C07D 413/12* (2006.01)

(52) U.S. Cl. .................... 514/423; 514/237.2; 514/356; 548/518; 544/141; 546/208

(58) Field of Classification Search ................ 514/423; 548/518; 544/141; 546/208
See application file for complete search history.

(56) References Cited

U.S. PATENT DOCUMENTS

| | | | | |
|---|---|---|---|---|
| 4,105,776 | A | 8/1978 | Ondetti et al. | 424/274 |
| 4,248,883 | A | 2/1981 | Sawayama et al. | 424/274 |
| 4,331,673 | A | 5/1982 | Crossley | 424/263 |
| 5,648,393 | A | 7/1997 | Stamler et al. | 514/562 |
| 5,852,047 | A | 12/1998 | Byrne et al. | 514/423 |
| 5,866,568 | A * | 2/1999 | Bradbury et al. | 514/227.8 |
| 6,218,417 | B1 | 4/2001 | Del Soldato | 514/398 |
| 6,242,432 | B1 | 6/2001 | Del Soldato | 514/89 |
| 6,433,182 | B1 | 8/2002 | Garvey et al. | 548/301.7 |
| 6,462,044 | B2 | 10/2002 | Garvey et al. | 514/246 |

FOREIGN PATENT DOCUMENTS

| | | |
|---|---|---|
| EP | 0 007 477 A | 2/1980 |
| JP | 11071279 A2 * | 3/1999 |
| WO | 90/02118 | 3/1990 |
| WO | 97/16405 | 5/1997 |
| WO | 98/21193 | 5/1998 |
| WO | WO 00/61537 | 10/2000 |
| WO | WO 00/61541 | 10/2000 |
| WO | WO 01/12584 A2 | 2/2001 |

OTHER PUBLICATIONS

Wanstall et al., "Vascular Smooth Muscle Relaxation Mediated by Nitric Oxide Donors: A Comparison with Acetylcholine, Nitric Oxide and Nitroxyl Ion", *Br. J. Pharmacol.* 134, 463–472, 2001.
*Martindale: The Complete Drug Reference*, 33rd Edition; Sweetman, S.C. (Ed.); Pharmaceutical Press; London, Chicago; 2002, pp. 823, 825.
*Goodman & Gilman's The Pharmacological Basis of Therapeutics*, 10th Edition, McGraw-Hill Medical Publishing Division, 2001, pp. 821–822.
WO 98/21193 published May 22, 1998.
WO 95/20571 published Aug. 3, 1995.
WO 99/00361 published Jan. 7, 1999.
WO 02/100400 A1 published Dec. 19, 2002.
Patent Abstracts of Japan, vol. 1999, No. 8, Jun. 30, 1999 & JP 11 071279 A Mar. 16, 1999.

* cited by examiner

*Primary Examiner*—Joseph K. McKane
*Assistant Examiner*—Nyeemah Grazier
(74) *Attorney, Agent, or Firm*—Arent Fox PLLC

(57) ABSTRACT

Captopril nitroderivatives having improved pharmacological activity and enhanced tolerability are described. They can be employed for the treatment or prophylaxis of cardiovascular, inflammatory and renal diseases.

24 Claims, No Drawings

CAPTOPRIL DERIVATIVES

The present invention relates to new captopril derivatives, pharmaceutical compositions containing them and their use for the treatment of cardiovascular, inflammatory, renal diseases and ocular hypertension.

Captopril (1-[(2S)-3-mercapto-2-methylpropionyl]-L-proline) is the first ACE (Angiotensin Converting Enzyme) inhibitor to be marketed. It is the only ACE inhibitor approved for use in the United States that contains a sulfhydryl moiety. ACE inhibitors are antihypertensive drugs that act as vasodilators and reduce peripheral resistance. They inhibit angiotensin converting enzyme (ACE), which is involved in the conversion of angiotensin I to angiotensin II. Angiotensin II stimulates the synthesis and secretion of aldosterone and raises blood pressure via a potent direct vasoconstrictor effect. ACE is identical to bradykininase (kininase II) an enzyme that inactivates bradykinin and ACE inhibitors may reduce the degradation of bradykinin, a potent vasodilator.

Captopril is used in the management of hypertension, in heart failure, following myocardial infarction and in diabetic nephropathy (Martindale, Thirty-third edition, pp. 823, 854).

Given orally, captopril is rapidly adsorbed and has a bioavailability of about 75%; it produces a maximum effect within 1 to 2 hours and most of the drug is eliminated in urine (Goodman & Gilman's, Tenth edition, McGraw-Hill, p. 821).

Now, it has been reported that captopril has side-effects such as for example hypotension, cough, hyperkalemia, acute renal failure, skin rash, proteinuria, angioedema, dysgeusia and neutropenia.

U.S. Pat. No. 6,242,432 discloses derivatives of formula $A\text{-}(X_1\text{---}NO_2)_{to}$ having an antithrombotic activity, wherein A is the residue of ACE inhibitors or Beta-Adrenergic Blockers, particularly enalapril or timolol, $X_1$ is a bivalent connecting bridge and $t_o$ is 1 or 2.

U.S. Pat. No. 6,218,417 discloses nitric salts of ACE inhibitors having platelet anti-aggregating activity and anti-hypertension activity having reduced bronchial side effects.

U.S. Pat. No. 6,462,044 discloses a pharmaceutical composition comprising the phosphodiesterase inhibitor and an S-nitrosothiol such as S-nitroso-captopril.

U.S. Pat. No. 6,433,182 discloses a method of treating a sexual dysfunction in a female individual in need thereof comprising administering to the female individual an amount of an α-adrenergic receptor antagonist and an S-nitrosothiol such as S-nitroso-captopril.

U.S. Pat. No. 5,648,393 describes a method for the treatment or prevention of impotence in a human male in need thereof, comprising treating or preventing impotence in a human male in need thereof by administering a corpus cavernosum nonvascular smooth muscle relaxing amount of an S-nitrosothiol such as S-nitroso-captopril.

U.S. Pat. No. 5,852,047 discloses pharmaceutical product comprising a salicylate of an esterifiable ACE inhibitor, especially captopril-S-aspirinate; U.S. Pat. No. 4,331,673 describes pyridinium salts of captopril.

WO 90/02118 discloses S-protected derivatives of captopril and its analogues and methods for their preparation.

It was an object of the present invention to provide new captopril derivatives having better effectiveness and tolerability, that are free from the above mentioned side effects and thus could be employed for the treatment or prophylaxis of cardiovascular, inflammatory, renal diseases and ocular hypertension.

In particular, it has been recognized that the captopril derivatives of the present invention can be employed for treating or preventing acute coronary syndromes, stroke, pulmonary and ocular hypertension, hypertension, diabetic nephropathy and peripheral vascular diseases.

Object of the present invention are therefore captopril nitro-derivatives and/or pharmaceutically acceptable salts or stereoisomers thereof of general formula (I):

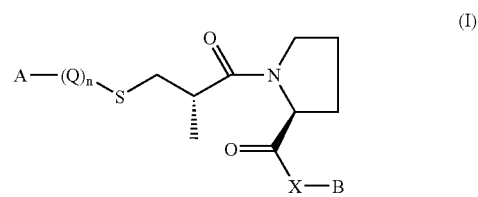

(I)

wherein:

Q=—CO—, —OCO—, —CONH—, —COCH(R)NH— wherein R is H, straight or branched $(C_1\text{--}C_6)$-alkyl, —$(CH_2)_2SCH_3$ or benzyl;

with the proviso that —S— is bound to —CO—;

n is an integer equal to 0 or 1;

A=H, W (wherein W is $C_1\text{--}C_6$-alkyl, phenyl or benzyl) or is chosen from the following groups:

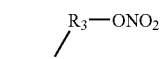

1a)

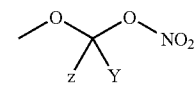

1b)

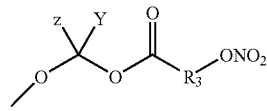

1c)

wherein z and Y are the same or different, and are H or straight or branched $(C_1\text{--}C_4)$-alkyl; with the proviso that when A is selected from the groups 1b and 1c, Q=—CO—;

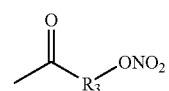

1d$_1$)

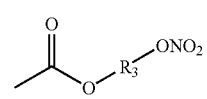

1d$_2$)

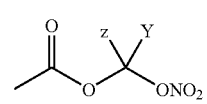

1d$_3$)

wherein z and Y are as above defined;

with the proviso that when A is selected from the groups 1d$_1$–1d$_3$, Q=—COCH(R)NH— wherein R is as above defined;

R₃ is a bivalent radical having the following meanings:
a) a straight or whenever possible branched $C_1$–$C_{20}$ alkylene, optionally substituted with at least an halogen atom, preferably having from 1 to 5 carbon atoms and or an optionally substituted cycloalkylene having from 5 to 7 carbon atoms;

b)
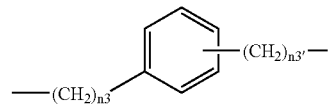

c)
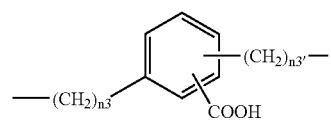

wherein:
n3 is an integer from 0 to 20, preferably from 0 to 5;
n3' is an integer from 1 to 20, preferably from 1 to 5;
wherein the —ONO₂ group is bound to a —CH₂ group;

d)
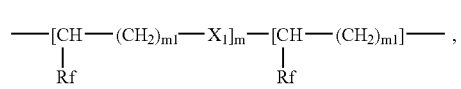

d1)
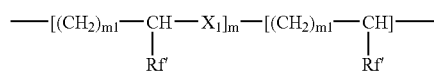

wherein $X_1$ is —O— or —S—, m is an integer from 1 to 6, preferably from 1 to 4, $m_1$ is an integer from 1 to 10, preferably from 1 to 5, Rf is a hydrogen atom or $CH_3$, Rf' is $CH_3$;

e)
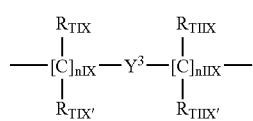

wherein:
nIX is an integer from 0 to 10, preferably from 0 to 3;
nIIX is an integer from 1 to 10, preferably from 1 to 3;
$R_{TIX}$, $R_{TIX'}$, $R_{TIIX}$, $R_{TIIX'}$, are the same or different, and are H
or straight or branched ($C_1$–$C_4$)-alkyl, preferably $R_{TIX}$, $R_{TIX'}$, $R_{TIIX}$, $R_{TIIX'}$ are H;
and wherein the —ONO₂ group is bound to

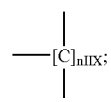

y³ è an heterocyclic saturated, unsaturated or aromatic 5 or 6 members ring, containing one or more heteroatoms selected from nitrogen, oxygen, sulphur, and selected for example from (Y1)
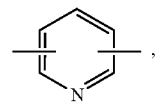

(Y2)
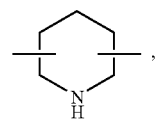

(Y3)
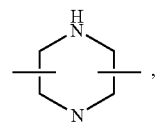

(Y4)
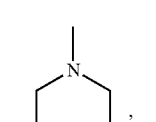

(Y5)
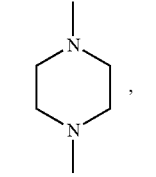

(Y6)
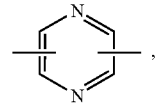

(Y7)
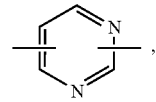

(Y8)
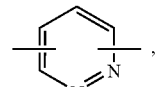

(Y9)
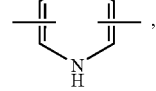

(Y10)
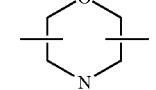

(Y11)
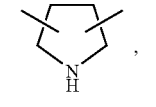

(Y12)
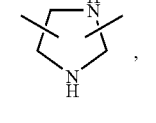

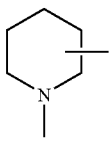
(Y13)

X=—NH—, —O—, —S—;
B=H, —$R_{3a}$—$ONO_2$ wherein $R_{3a}$ has the same meaning of $R_3$ as above defined or is chosen from the following groups:

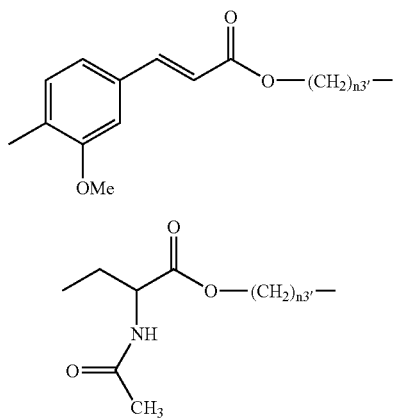

f)

g)

wherein n3' is as above defined; and wherein the —$ONO_2$ group is bound to the group —$(CH_2)_{n3'}$; or B is the group of formula (IA):

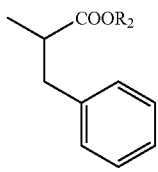

(IA)

wherein $R_2$ is H, a straight or branched ($C_1$–$C_6$)-alkyl or —$R_{3b}$—$ONO_2$ wherein $R_{3b}$ has the same meaning of $R_3$ as above defined in a);

Provided that:
i) when $R_{3a}$ is the group as defined in f) and g) then A is W;
ii) when $R_{3a}$ is the group as defined in g) then X is —S—;
iii) when B is the group of formula (IA) then X is —NH—;
iv) at least one of the groups A or B contains a —$ONO_2$ group. The term "($C_1$–$C_6$)-alkyl" as used herein refers to branched or straight chain alkyl groups comprising one to six carbon atoms, including methyl, ethyl, propyl, isopropyl, n-butyl, t-butyl and the like. The term "$C_1$–$C_{20}$ alkylene" as used herein refers to branched or straight chain $C_1$–$C_{20}$ hydrocarbon, preferably having from 2 to 5 carbon atoms such as ethylene, propylene, butylene, pentylene.

The term "halogen atom" as used herein refers to chloro, bromo or fluoro atoms.

The term "cycloalkylene" as used herein refers to ring having from 5 to 7 carbon atoms including, but not limited to, cyclopentylene, cyclohexylene optionally substituted with side chains such as straight or branched ($C_1$–$C_{10}$)-alkyl, preferably $CH_3$.

The term "heterocyclic" as used herein refers to saturated, unsaturated or aromatic 5 or 6 members ring, containing one or more heteroatoms selected from nitrogen, oxygen, sulphur, such as for example pyridine, pyrazine, pyrimidine, pyrrolidine, morpholine, imidazole and the like.

As already said, the invention includes also the pharmaceutically acceptable salts of the compounds of formula (I).

Examples of pharmaceutically acceptable salts are either those with inorganic bases, such as sodium, potassium, calcium and aluminium hydroxides, or with organic bases, such as lysine, arginine, triethylamine, dibenzylamine, piperidine and other acceptable organic amines.

Another aspect of the present invention provides the use of the compounds of formula (I) in combination with at least a compounds used to treat cardiovascular disease selected from the group consisting of: beta adrenergic blokers, calcium channel blockers, angiotensin II receptor antagonists, antithrombotics, HMGCoA reductase inhibitors, aspirin or nitrooxyderivatives of aspirin, nitrosated beta blockers, nitrosated or nitrosilated calcium channel blockers.

The present invention also provides pharmaceutical kits comprising one or more containers filled with one or more of the compounds and or compositions of the present invention and one or more of the compounds used to treat cardiovascular disease reported above.

Suitable beta adrenergic blokers, calcium channel blockers, angiotensin II receptor antagonists, antithrombotics, are described in the literature such as The Merck Index (13th edition).

Suitable nitrosated beta adrenergic blokers and nitrooxyderivatives of aspirin are disclosed respectively in WO 98/21193 and WO97/16405.

The compounds according to the present invention, when they contain in the molecule one salifiable nitrogen atom, can be transformed into the corresponding salts by reaction in organic solvent such as acetonitrile, tetrahydrofuran with the corresponding organic or inorganic acid.

Examples of organic acids are: oxalic, tartaric, maleic, succinic, citric acid.

Examples of inorganic acids are: nitric, hydrochloric, sulphuric, phosphoric acid.

Salts with nitric acid are preferred.

The compounds of the invention which have one or more asymmetric carbon atoms can exist as the optically pure enantiomers, pure diastereomers, enantiomers mixtures, diastereomers mixtures, enantiomer racemic mixtures, racemates or racemate mixtures. Within the object of the invention are also all the possible isomers, stereoisomers and their mixtures of the compounds of formula (I).

Preferred compounds are those of formula (I) wherein:
Q=—CO—, —OCO—, —CONH—, —COCH(R)NH— wherein R is H or $CH_3$; with the proviso that —S— is bound to —CO;
n is an integer equal to 0 or 1;
A=H, W (wherein W is $C_1$–$C_6$-alkyl preferably $CH_3$) or is chosen from the following groups:

1a)
$R_3$—$ONO_2$

-continued

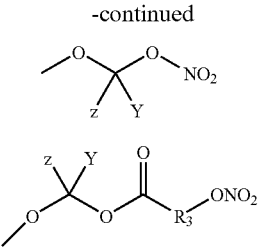
1b)

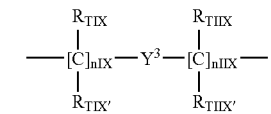
e)

wherein z and Y are the same or different, and are H or CH₃; with the proviso that when A is selected from the groups 1b and 1c, Q=—CO—;

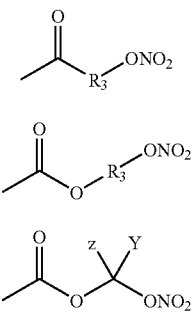
1d₁)
1d₂)
1d₃)

wherein:
nIX is an integer from 0 to 3 and nIIX is an integer from 1 to 3;
$R_{TIX}$, $R_{TIX'}$, $R_{TIIX}$, $R_{TIIX'}$ are the same and are H;
and wherein the —ONO₂ group is bound to a —CH₂ group;
$Y^3$ è an heterocyclic saturated, unsaturated or aromatic, containing one or more atoms of nitrogen and selected from Y1–Y6 as defined in claim 1;
X=—NH—, —O—, —S—;
B=H, —$R_{3a}$—ONO₂ wherein $R_{3a}$ has the same meaning of $R_3$ as above defined or is chosen from the following groups:

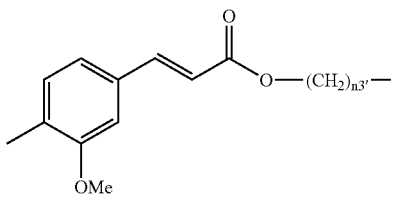
f)

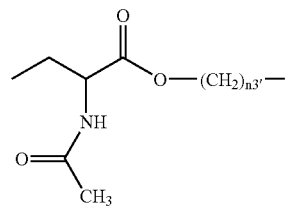
g)

wherein z and Y are as above defined;
with the proviso that when A is selected from groups 1d₁–1d₃, Q=—COCH(R)NH— wherein R is as above defined;
$R_3$ is a bivalent radical having the following meanings:
a) straight $C_1$–$C_6$ alkylene, preferably $C_3$–$C_5$ alkylene;

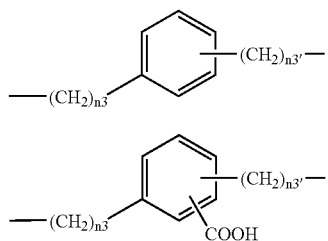
b)
c)

wherein:
n3 is an integer from 0 to 5 and n3' is an integer from 1 to 5;
wherein the —ONO₂ group is bound to a —CH₂ group;

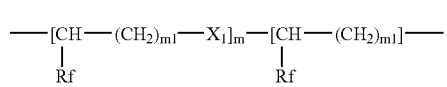
d)

wherein $X_1$ is —O—, m is an integer from 1 to 4, preferably 1, $m_1$ is an integer from 1 to 5, preferably 1, Rf is a hydrogen atom or CH₃;

wherein n3' is as above defined, preferably 4; wherein the —ONO₂ group is bound to the group —(CH₂)$_{n3'}$; or B is the group of formula (IA):

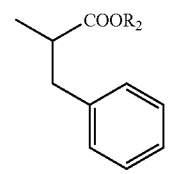
(IA)

wherein $R_2$ is H, a straight or branched ($C_1$–$C_6$)-alkyl or —$R_{3b}$—ONO₂ wherein $R_{3b}$ has the same meaning of $R_3$ as above defined in a);
Preferred compounds of formula (I) according to the present invention are the following:
(1) A compound of formula (I) wherein Q=—CO—, n=1, A is the group as defined in 1a) wherein $R_3$ is a straight $C_3$ alkylene, X=—O— and B is H:

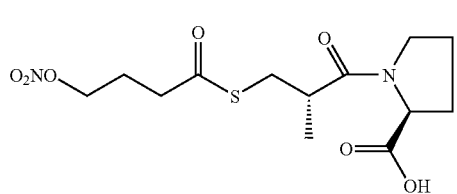

(2) A compound of formula (I) wherein Q=—CO—, n=1, A is the group as defined in 1a) wherein $R_3$ is a straight $C_4$ alkylene, X=—O— and B is H:

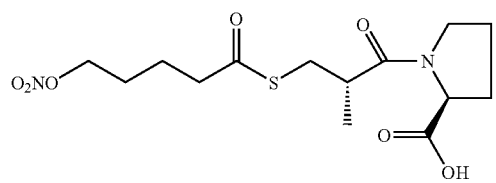

(3) A compound of formula (I) wherein Q=—CO—, n=1, A is the group as defined in 1a) wherein $R_3$ is the group as defined in b) wherein n3 is an integer equal to 0 and n3' is an integer equal to 1, X=—O— and B is H:

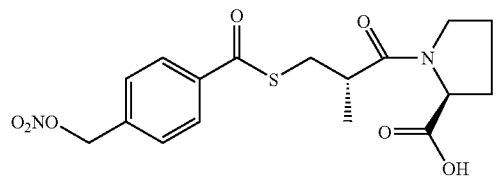

(4) A compound of formula (I) wherein Q=—OCO—, n=1, A is the group as defined in 1a) wherein $R_3$ is a straight $C_4$ alkylene, X=—O— and B is H:

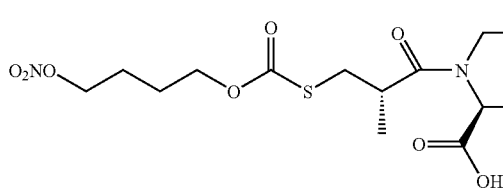

(5) A compound of formula (I) wherein Q=—OCO—, n=1, A is the group as defined in 1a) wherein $R_3$ is a straight $C_3$ alkylene, X=—O— and B is H:

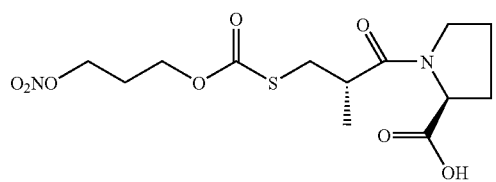

(6) A compound of formula (I) wherein Q=—OCO—, n=1, A is the group as defined in 1a) wherein $R_3$ is the group as defined in b) wherein n3 is an integer equal to 0 and n3' is an integer equal to 1, X=—O— and B is H:

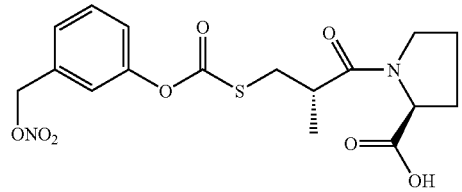

(7) A compound of formula (I) wherein Q=—CO—, n=1, A is the group as defined in 1b) wherein z is H and Y is $CH_3$, X=—O— and B is H:

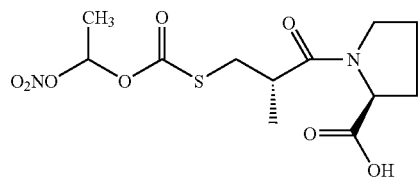

(8) A compound of formula (I) wherein Q=—CO—, n=1, A is the group as defined in 1b) wherein z and Y are H, X=—O— and B is H:

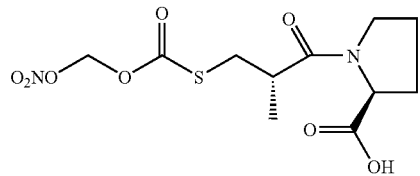

(9) A compound of formula (I) wherein Q=—CO—, n=1, A is the group as defined in 1c) wherein z and Y are H, $R_3$ is the group as defined in b) wherein n3 is an integer equal to 0 and n3' is an integer equal to 1, X=—O— and B is H:

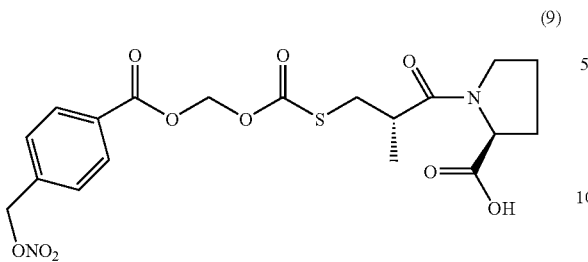
(9)

(10) A compound of formula (I) wherein Q=—COCH(R)NH— with R=CH$_3$, n=1, A is the group as defined in 1d$_1$) wherein R$_3$ is a straight C$_4$ alkylene, X=—O— and B is H:

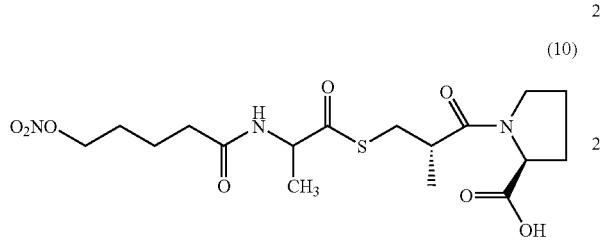
(10)

(11) A compound of formula (I) wherein Q=—COCH(R)NH— with R=CH$_3$, n=1, A is the group as defined in 1d$_1$) wherein R$_3$ is a straight C$_3$ alkylene, X=—O— and B is H:

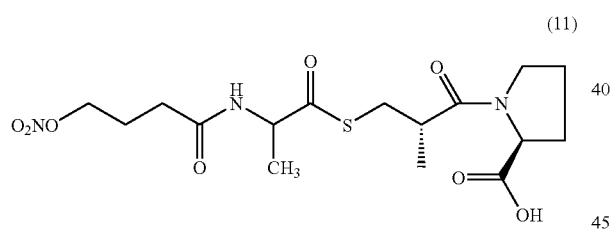
(11)

(12) A compound of formula (I) wherein Q=—COCH(R)NH— with R=H, n=1, A is the group as defined in 1d$_1$) wherein R$_3$ is a straight C$_3$ alkylene, x=—O— and B is H:

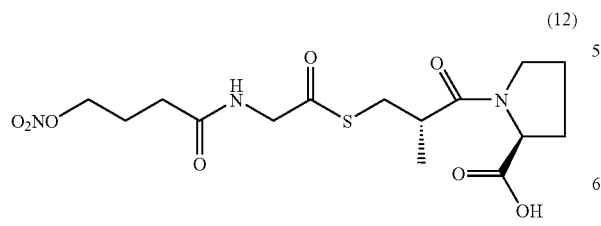
(12)

(13) A compound of formula (I) wherein Q=—COCH(R)NH— with R=H, n=1, A is the group as defined in 1d$_1$) wherein R$_3$ is a straight C$_4$ alkylene, X=—O— and B is H:

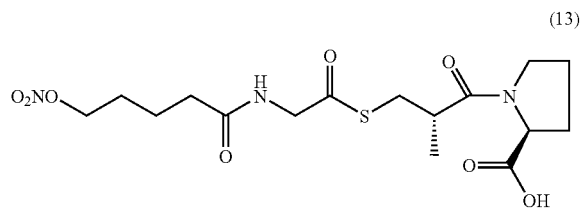
(13)

(14) A compound of formula (I) wherein Q=—COCH(R)NH— with R=CH$_3$, n=1, A is the group as defined in 1d$_1$) wherein R$_3$ is the group as defined in b) wherein n3 is an integer equal to 0 and n3' is an integer equal to 1, X=—O— and B is H:

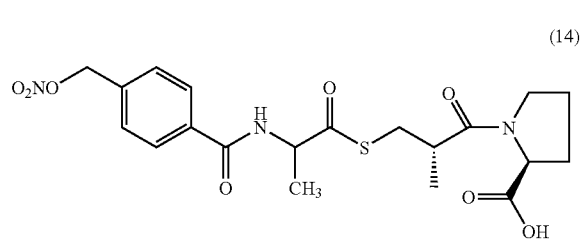
(14)

(15) A compound of formula (I) wherein Q=—COCH(R)NH— with R=H, n=1, A is the group as defined in 1d$_1$) wherein R$_3$ is the group as defined in b) wherein n3 is an integer equal to 0 and n3' is an integer equal to 1, X=—O— and B is H:

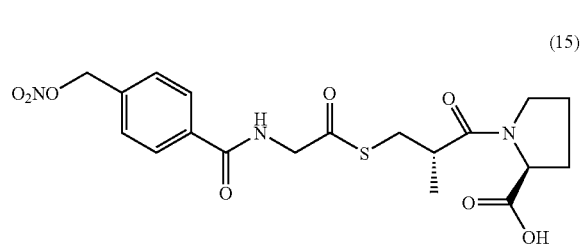
(15)

(16) A compound of formula (I) wherein Q=—COCH(R)NH— with R=CH$_3$, n=1, A is the group as defined in 1d$_2$) wherein R$_3$ is a straight C$_4$ alkylene, X=—O— and B is H:

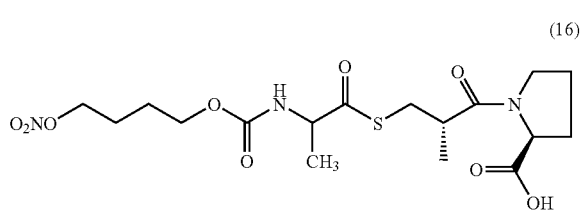
(16)

(17) A compound of formula (I) wherein Q=—COCH(R)NH— with R=CH$_3$, n=1, A is the group as defined in 1d$_2$) wherein R$_3$ is a straight C$_3$ alkylene, X=—O— and B is H:

(17)

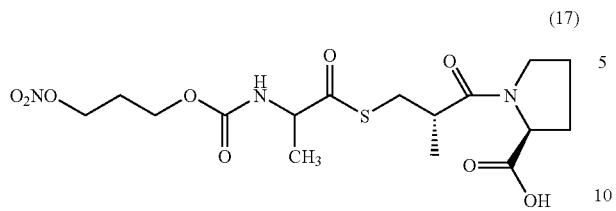

(18) A compound of formula (I) wherein Q=—COCH(R)NH— with R=CH₃, n=1, A is the group as defined in 1d₃) wherein z is H and Y is CH₃, X=—O— and B is H:

(18)

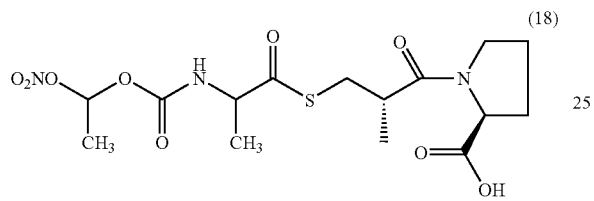

(19) A compound of formula (I) wherein Q=—COCH(R)NH— with R=CH₃, n=1, A is the group as defined in 1d₃) wherein z and Y are H, X=—O— and B is H:

(19)

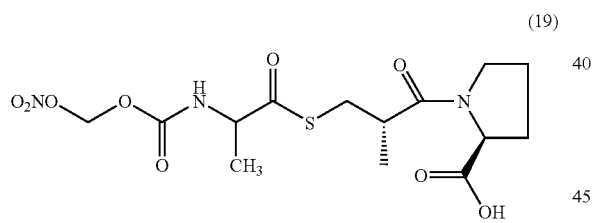

(20) A compound of formula (I) wherein Q=—COCH(R)NH— with R=H, n=1, A is the group as defined in 1d₂) wherein R₃ is a straight C₄ alkylene, X=—O— and B is H:

(20)

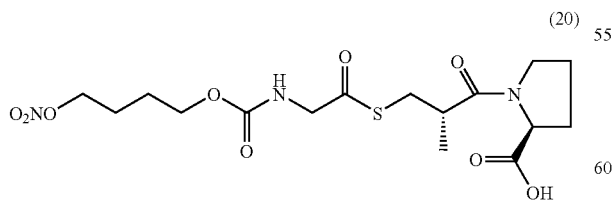

(21) A compound of formula (I) wherein Q=—COCH(R)NH— with R=H, n=1, A is the group as defined in 1d₂) wherein R₃ is a straight C₃ alkylene, X=—O— and B is H:

(21)

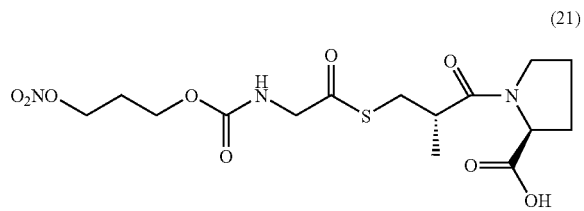

(22) A compound of formula (I) wherein Q=—COCH(R)NH— with R=H, n=1, A is the group as defined in 1d₃) wherein z is H and Y is CH₃, X=—O— and B is H:

(22)

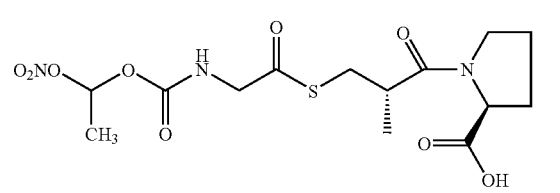

(23) A compound of formula (I) wherein Q=—COCH(R)NH— with R=H, n=1, A is the group as defined in 1d₃) wherein z and Y are H, X=—O— and B is H:

(23)

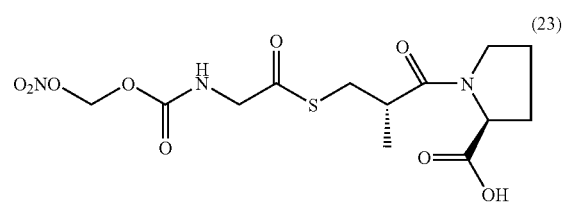

(24) A compound of formula (I) wherein Q=—COCH(R)NH— with R=CH₃, n=1, A is the group as defined in 1d₂) wherein R₃ is the group as defined in b) wherein n3 is an integer equal to 0 and n3' is an integer equal to 1, X=—O— and B is H:

(24)

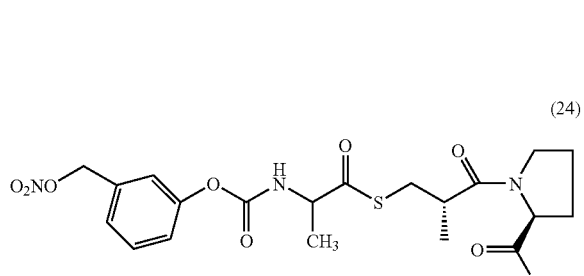

(25) A compound of formula (I) wherein Q=—COCH(R)NH— with R=H, n=1, A is the group as defined in 1d$_2$) wherein R$_3$ is the group as defined in b) wherein n3 is an integer equal to 0 and n3' is an integer equal to 1, X=—O— and B is H:

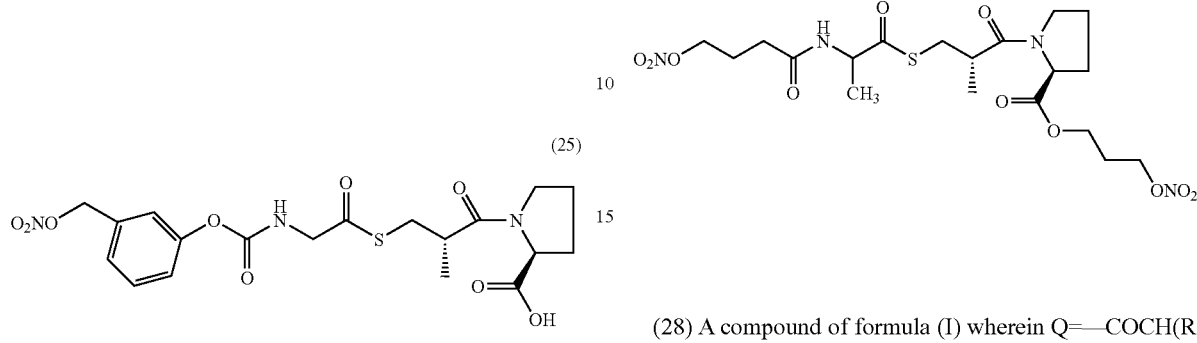

(25)

(26) A compound of formula (I) wherein Q=—COCH(R)NH— with R=CH$_3$, n=1, A is the group as defined in 1d$_1$) wherein R$_3$ is a straight C$_4$ alkylene, X=—O— and B=—R$_{3a}$—ONO$_2$ wherein R$_{3a}$ is a straight C$_3$ alkylene:

(26)

(27) A compound of formula (I) wherein Q=—COCH(R)NH— with R=CH$_3$, n=1, A is the group as defined in 1d$_1$) wherein R$_3$ is a straight C$_3$ alkylene, X=—O— and B=—R$_{3a}$—ONO$_2$ wherein R$_{3a}$ is a straight C$_3$ alkylene:

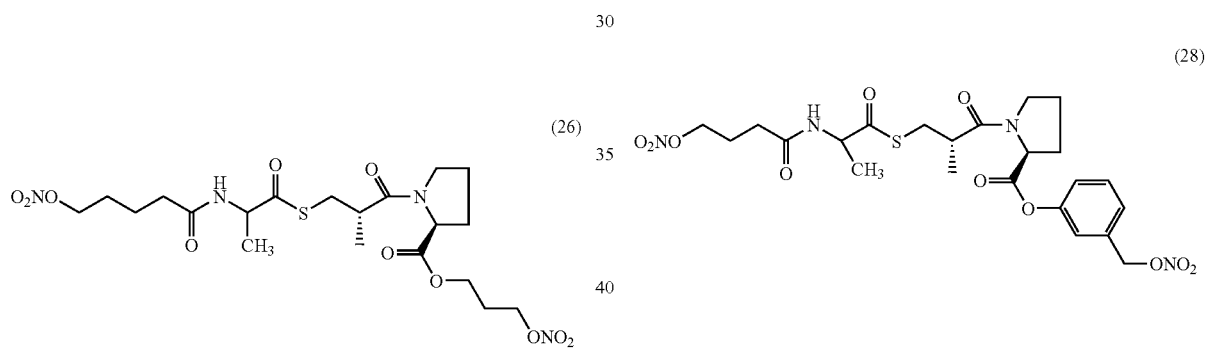

(27)

(28) A compound of formula (I) wherein Q=—COCH(R)NH— with R=CH$_3$, n=1, A is the group as defined in 1d$_1$) wherein R$_3$ is a straight C$_3$ alkylene, X=—O— and B=—R$_{3a}$—ONO$_2$ wherein R$_{3a}$ is the group as defined in b) wherein n3 is an integer equal to 0 and n3' is an integer equal to 1:

(28)

(29) A compound of formula (I) wherein Q=—COCH(R)NH— with R=CH$_3$, n=1, A is the group as defined in 1d$_1$) wherein R$_3$ is a straight C$_4$ alkylene, X=—O— and B=—R$_{3a}$—ONO$_2$ wherein R$_{3a}$ is the group as defined in b) wherein n3 is an integer equal to 0 and n3' is an integer equal to 1:

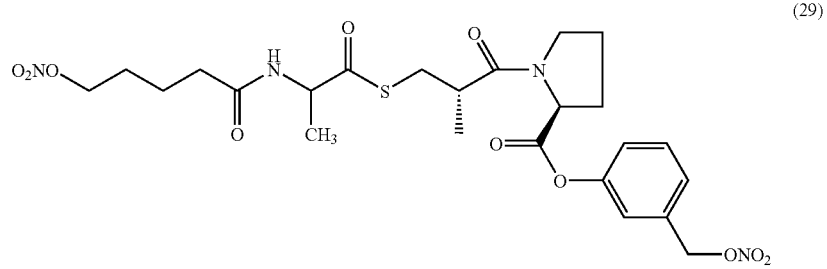

(29)

(30) A compound of formula (I) wherein Q=—COCH(R)NH— with R=H, n=1, A is the group as defined in 1d$_1$) wherein R$_3$ is a straight C$_4$ alkylene, X=—O— and B=—R$_{3a}$—ONO$_2$ wherein R$_{3a}$ is a straight C$_3$ alkylene:

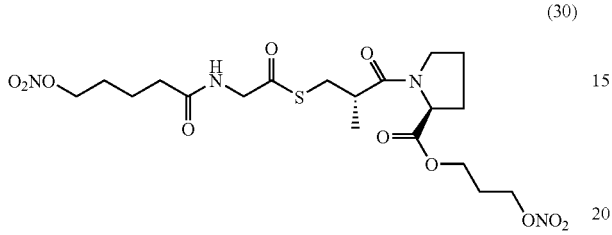

(30)

(31) A compound of formula (I) wherein Q=—COCH(R)NH— with R=H, n=1, A is the group as defined in 1d$_1$) wherein R$_3$ is a straight C$_3$ alkylene, X=—O— and B=—R$_{3a}$—ONO$_2$ wherein R$_{3a}$ is a straight C$_3$ alkylene:

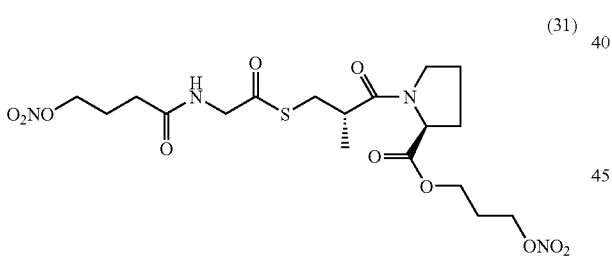

(31)

(32) A compound of formula (I) wherein Q=—COCH(R)NH— with R=H, n=1, A is the group as defined in 1d$_1$) wherein R$_3$ is a straight C$_3$ alkylene, X=—O— and B=—R$_{3a}$—ONO$_2$ wherein R$_{3a}$ is the group as defined in b) wherein n3 is an integer equal to 0 and n3' is an integer equal to 1:

(32)

(33) A compound of formula (I) wherein Q=—COCH(R)NH— with R=H, n=1, A is the group as defined in 1d$_1$) wherein R$_3$ is a straight C$_4$ alkylene, X=—O— and B=—R$_{3a}$—ONO$_2$ wherein R$_{3a}$ is the group as defined in b) wherein n3 is an integer equal to 0 and n3' is an integer equal to 1:

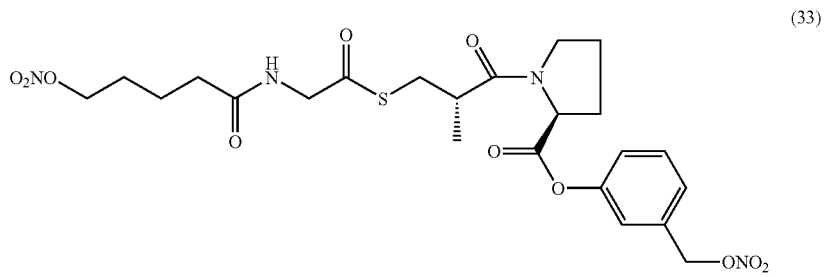

(33)

(34) A compound of formula (I) wherein Q=—COCH(R)NH— with R=CH$_3$, n=1, A is the group as defined in 1d$_1$) wherein R$_3$ is a straight C$_4$ alkylene, X=—O— and B=—R$_{3a}$—ONO$_2$ wherein R$_{3a}$ is a straight C$_4$ alkylene:

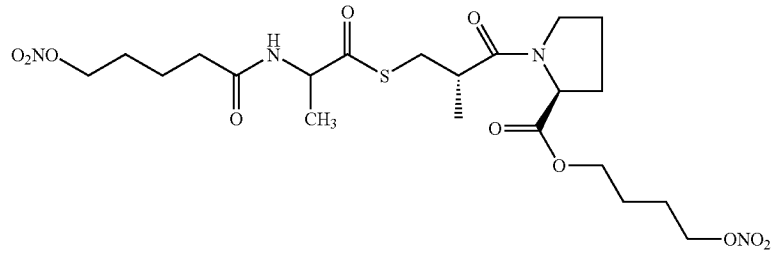

(34)

(35) A compound of formula (I) wherein Q=—COCH(R)NH— with R=H, n=1, A is the group as defined in 1d$_1$) wherein R$_3$ is a straight C$_4$ alkylene, X=—O— and B=—R$_{3a}$—ONO$_2$ wherein R$_{3a}$ is a straight C$_4$ alkylene:

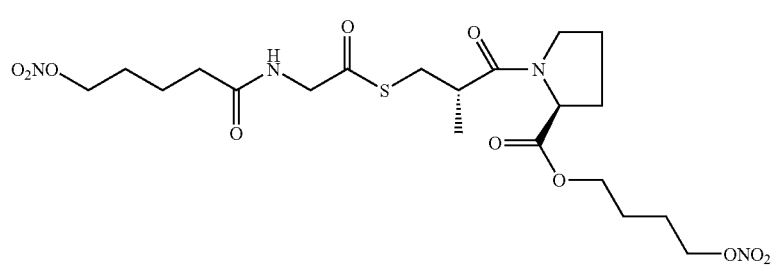

(35)

(36) A compound of formula (I) wherein Q=—COCH(R)NH— with R=CH$_3$, n=1, A is the group as defined in 1d$_1$) wherein R$_3$ is a straight C$_3$ alkylene, X=—O— and B=—R$_{3a}$—ONO$_2$ wherein R$_{3a}$ is a straight C$_4$ alkylene:

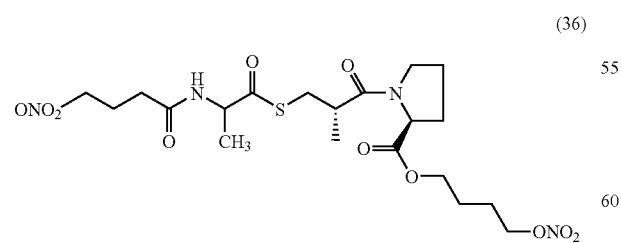

(36)

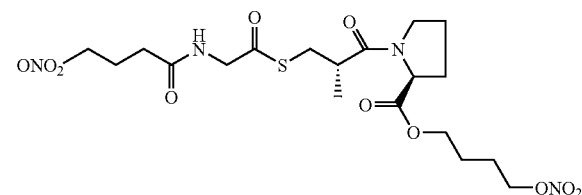

(37)

(37) A compound of formula (I) wherein Q=—COCH(R)NH— with R=H, n=1, A is the group as defined in 1d$_1$) wherein R$_3$ is a straight C$_3$ alkylene, X=—O— and B=—R$_{3a}$—ONO$_2$ wherein R$_{3a}$ is a straight C$_4$ alkylene:

(38) A compound of formula (I) wherein Q=—COCH(R)NH— with R=CH$_3$, n=1, A is H, X=—O— and B=—R$_{3a}$—ONO$_2$ wherein R$_{3a}$ is a straight C$_4$ alkylene:

(38)

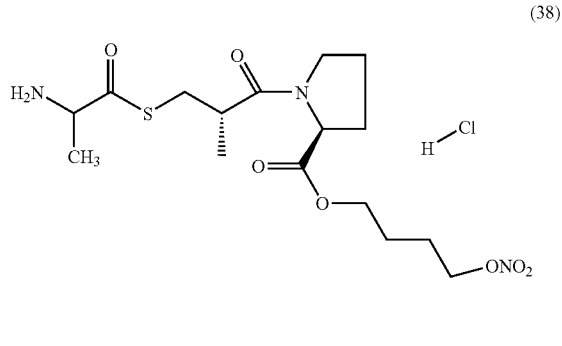

(39) A compound of formula (I) wherein Q=—COCH(R)NH— with R=CH$_3$, n=1, A is H, X=—O— and B=—R$_{3a}$—ONO$_2$ wherein R$_{3a}$ is a straight C$_3$ alkylene:

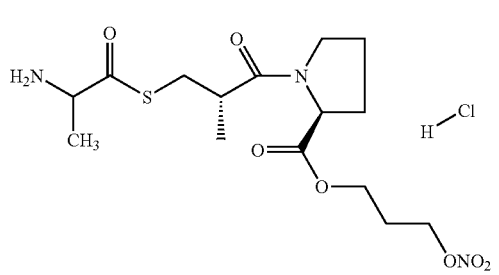
(39)

(40) A compound of formula (I) wherein Q=—COCH(R)NH— with R=CH$_3$, n=1, A is H, X=—O— and B=—R$_{3a}$—ONO$_2$ wherein R$_{3a}$ is the group as defined in b) wherein n3 is an integer equal to 0 and n3' is an integer equal to 1:

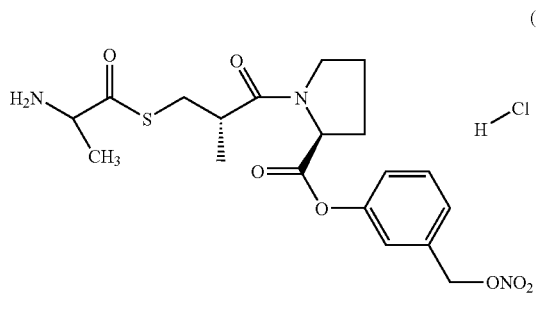
(40)

(41) A compound of formula (I) wherein Q=—COCH(R)NH— with R=CH$_3$, n=1, A is H, X=—O— and B=—R$_{3a}$—ONO$_2$ wherein R$_{3a}$ is the group as defined in b) wherein n3 and n3' are an integer equal to 1:

(41)

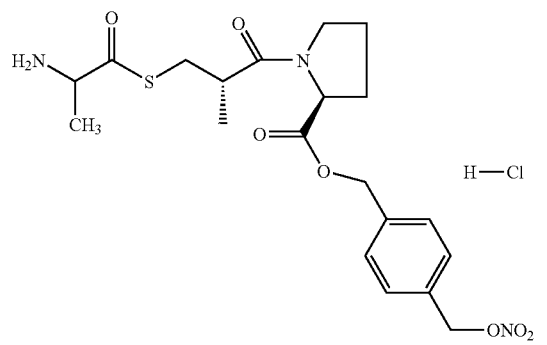

(42) A compound of formula (I) wherein Q=—COCH(R)NH— wherein R and A are H, n=1, X=—O— and B=—R$_{3a}$—ONO$_2$ wherein R$_{3a}$ is a straight C$_3$ alkylene:

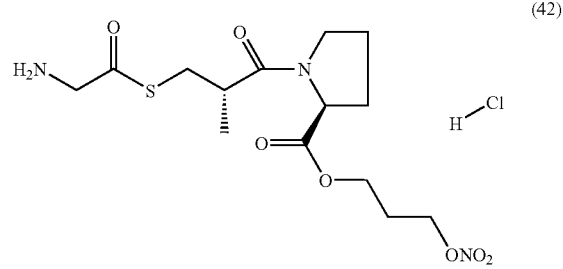
(42)

(43) A compound of formula (I) wherein Q=—COCH(R)NH— wherein R and A are H, n=1, X=—O— and B=—R$_{3a}$—ONO$_2$ wherein R$_{3a}$ is a straight C$_4$ alkylene:

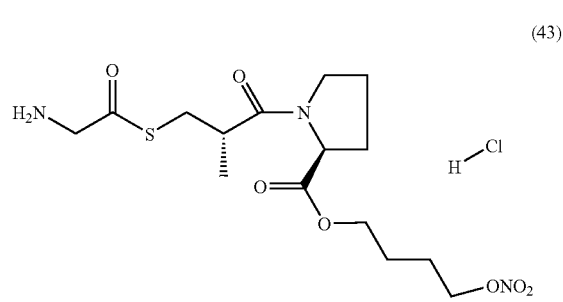
(43)

(44) A compound of formula (I) wherein Q=—COCH(R)NH— wherein R and A are H, n=1, X=—O— and B=—R$_{3a}$—ONO$_2$ wherein R$_{3a}$ is the group as defined in b) wherein n3 is an integer equal to 0 and n3' is an integer equal to 1:

(44)

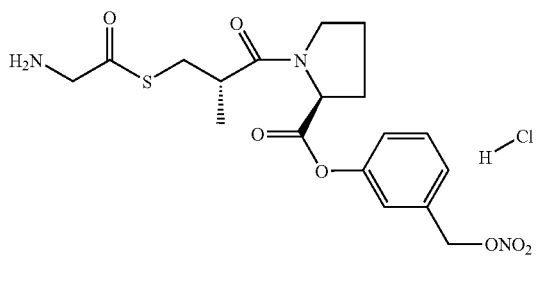

(45) A compound of formula (I) wherein Q=—COCH(R)NH— wherein R and A are H, n=1, X=—O— and B=—R$_{3a}$—ONO$_2$ wherein R$_{3a}$ is the group as defined in b) wherein n3 and n3' are an integer equal to 1:

(45)

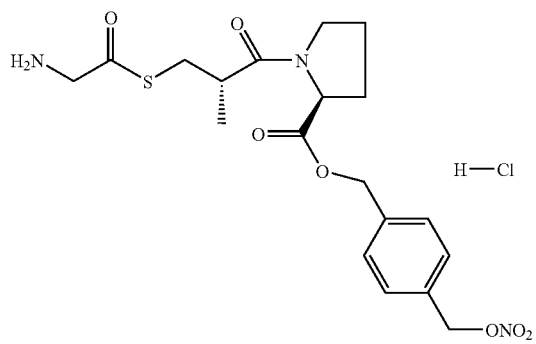

(46) A compound of formula (I) wherein Q=—CO—, n=1, A is the group as defined in 1a) wherein R$_3$ is a straight C$_3$ alkylene, X=—O— and B is =—R$_{3a}$—ONO$_2$ wherein R$_{3a}$ is a straight C$_3$ alkylene:

(46)

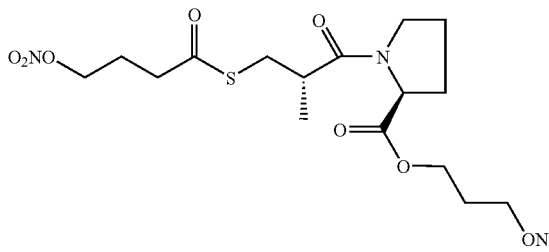

(47) A compound of formula (I) wherein Q=—CO—, n=1, A is the group as defined in 1a) wherein R$_3$ is a straight C$_3$ alkylene, X=—O— and B is =—R$_{3a}$—ONO$_2$ wherein R$_{3a}$ is a straight C$_4$ alkylene:

(47)

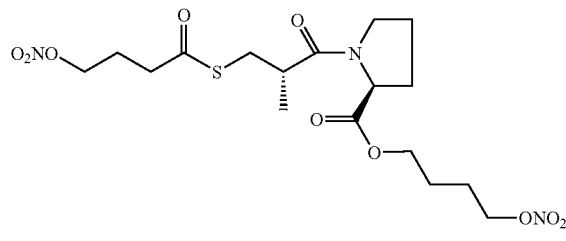

(48) A compound of formula (I) wherein Q=—CO—, n=1, A is the group as defined in 1a) wherein R$_3$ is a straight C$_3$ alkylene, X=—O— and B is =—R$_{3a}$—ONO$_2$ wherein R$_{3a}$ is the group as defined in b) wherein n3 is an integer equal to 0 and n3' is an integer equal to 1:

(48)

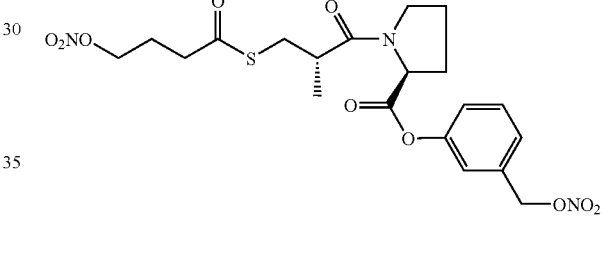

(49) A compound of formula (I) wherein Q=—CO—, n=1, A is the group as defined in 1a) wherein R$_3$ is a straight C$_4$ alkylene, X=—O— and B is =—R$_{3a}$—ONO$_2$ wherein R$_{3a}$ is the group as defined in b) wherein n3 is an integer equal to 0 and n3' is an integer equal to 1:

(49)

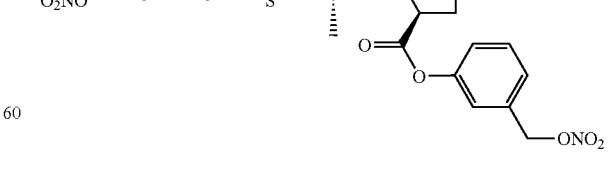

(50) A compound of formula (I) wherein Q=—CO—, n=1, A is the group as defined in 1a) wherein R$_3$ is a straight C$_4$ alkylene, X=—O— and B is =—R$_{3a}$—ONO$_2$ wherein R$_{3a}$ is a straight C$_4$ alkylene:

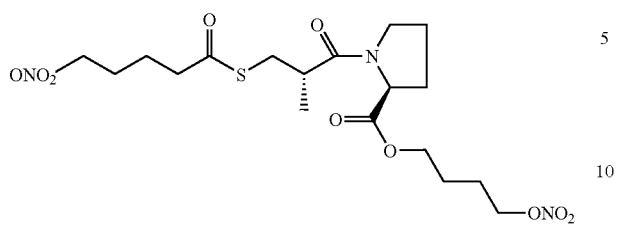

(51) A compound of formula (I) wherein Q=—CO—, n=1, A is the group as defined in 1a) wherein $R_3$ is a straight $C_4$ alkylene, X=—O— and B is =—$R_{3a}$—$ONO_2$ wherein $R_{3a}$ is a straight $C_3$ alkylene:

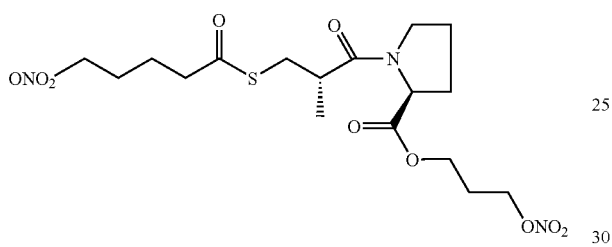

(52) A compound of formula (I) wherein Q=—OCO—, n=1, A is the group as defined in 1a) wherein $R_3$ is a straight $C_3$ alkylene, X=—O— and B is =—$R_{3a}$—$ONO_2$ wherein $R_{3a}$ is a straight $C_3$ alkylene:

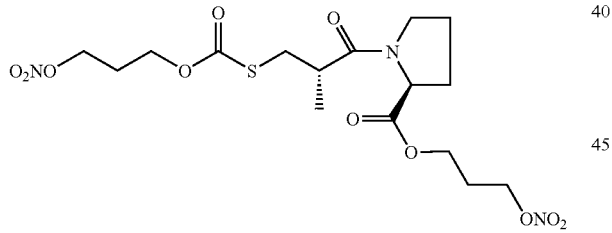

(53) A compound of formula (I) wherein Q=—OCO—, n=1, A is the group as defined in 1a) wherein $R_3$ is a straight $C_4$ alkylene, X=—O— and B is =—$R_{3a}$—$ONO_2$ wherein $R_{3a}$ is a straight $C_4$ alkylene:

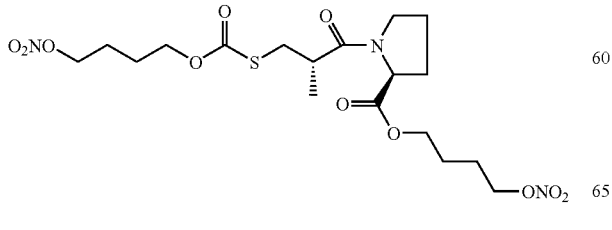

(54) A compound of formula (I) wherein Q=—OCO—, n=1, A is the group as defined in 1a) wherein $R_3$ is a straight $C_3$ alkylene, X=—O— and B is =—$R_{3a}$—$ONO_2$ wherein $R_{3a}$ is the group as defined in b) wherein n3 is an integer equal to 0 and n3' is an integer equal to 1:

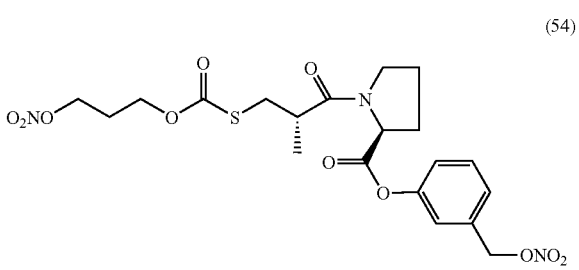

(55) A compound of formula (I) wherein Q=—OCO—, n=1, A is the group as defined in 1a) wherein $R_3$ is a straight $C_4$ alkylene, X=—O— and B is =—$R_{3a}$—$ONO_2$ wherein $R_{3a}$ is the group as defined in b) wherein n3 is an integer equal to 0 and n3' is an integer equal to 1:

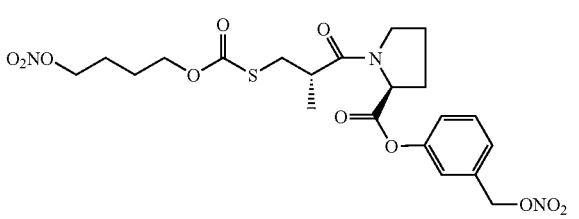

(56) A compound of formula (I) wherein Q=—OCO—, n=1, A is the group as defined in 1a) wherein $R_3$ is a straight $C_3$ alkylene, X=—O— and B is =—$R_{3a}$—$ONO_2$ wherein $R_{3a}$ is a straight $C_4$ alkylene:

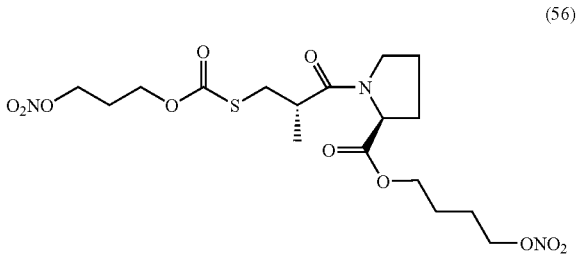

(57) A compound of formula (I) wherein Q=—OCO—, n=1, A is the group as defined in 1a) wherein $R_3$ is a straight $C_4$ alkylene, X=—O— and B is =—$R_{3a}$—$ONO_2$ wherein $R_{3a}$ is a straight $C_3$ alkylene:

(57)

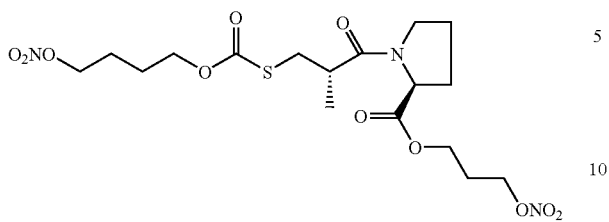

(58) A compound of formula (I) wherein Q=—CO—, n=1, A=W wherein W is CH$_3$, X=—O— and B is =R$_{3a}$—ONO$_2$ wherein R$_{3a}$ is a straight C$_4$ alkylene;

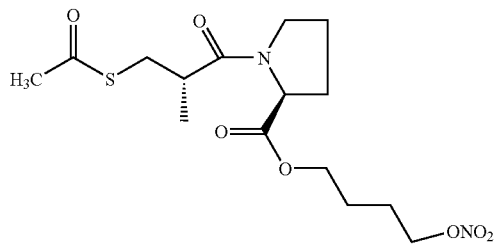

(59) A compound of formula (I) wherein Q=—CO—, n=1, A=W wherein W is CH$_3$, X=—O— and B is =—R$_{3a}$—ONO$_2$ wherein R$_{3a}$ is a straight C$_3$ alkylene:

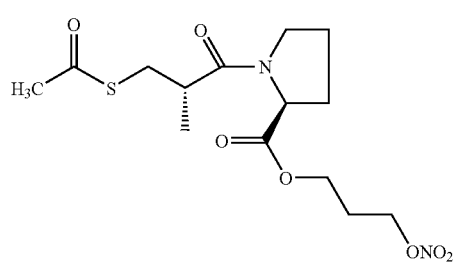

(60) A compound of formula (I) wherein Q=—CO—, n=1, A=W wherein W is CH$_3$, X=—O— and B is =R$_{3a}$—ONO$_2$ wherein R$_{3a}$ is the group as defined in b) wherein n3 is an integer equal to 0 and n3' is an integer equal to 1:

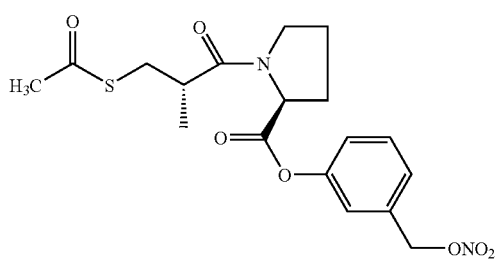

(61) A compound of formula (I) wherein Q=—CO—, n=1, A=W wherein W is CH$_3$, X=—O— and B is =R$_{3a}$—ONO$_2$ wherein R$_{3a}$ is the group as defined in b) wherein n3 and n3' are an integer equal to 1:

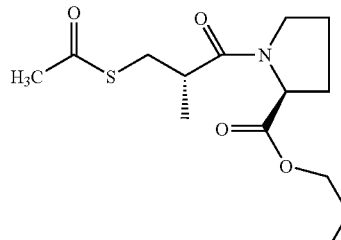

(62) A compound of formula (I) wherein Q=—CO—, n=1, A is the group as defined in 1b) wherein z and Y are H, X=—O— and B is =—R$_{3a}$—ONO$_2$ wherein R$_{3a}$ is a straight C$_3$ alkylene:

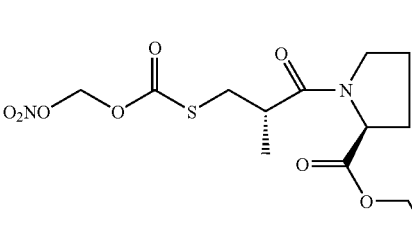

(63) A compound of formula (I) wherein Q=—CO—, n=1, A is the group as defined in 1b) wherein z is H and Y is CH$_3$, X=—O— and B is =—R$_{3a}$—ONO$_2$ wherein R$_{3a}$ is a straight C$_3$ alkylene:

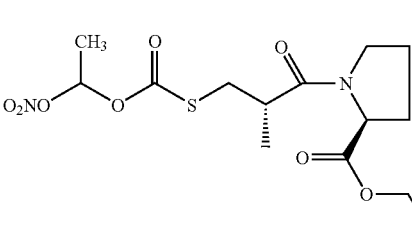

(64) A compound of formula (I) wherein Q=—CO—, n=1, A is the group as defined in 1b) wherein z and Y are H, X=—O— and B is =—R$_{3a}$—ONO$_2$ wherein R$_{3a}$ is a straight C$_4$ alkylene:

(64)

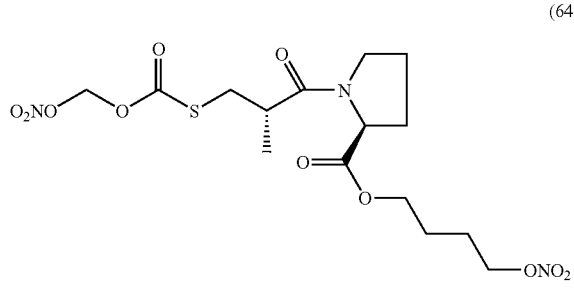

(67)

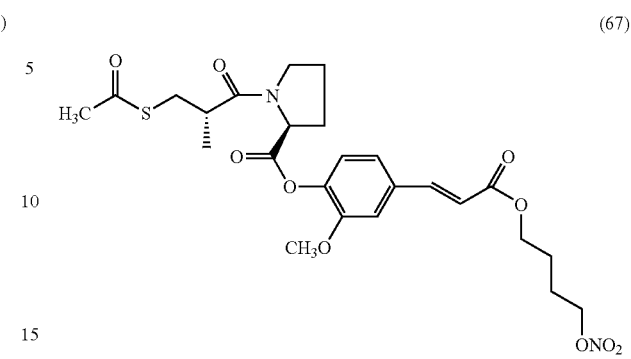

(65) A compound of formula (I) wherein Q=—CO—, n=1, A is the group as defined in 1b) wherein z is H and Y is CH₃, X=—O— and B is =—R₃ₐ—ONO₂ wherein R₃ₐ is a straight C₄ alkylene:

(68) A compound of formula (I) wherein Q=—CO—, n=1, A is the group as defined in 1a) wherein R₃ is a straight C₄ alkylene, X=—NH— and B is the group of formula (IA) wherein R₂ is H:

(65)

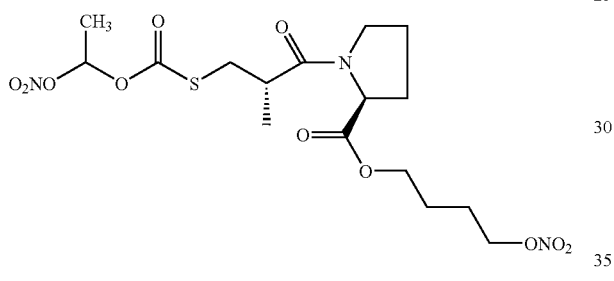

(68)

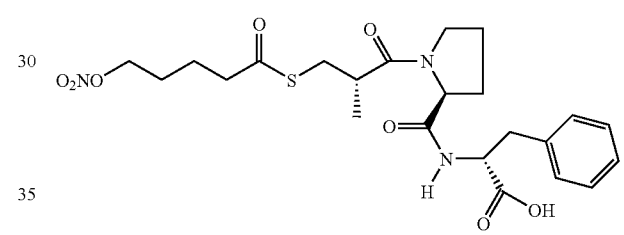

(66) A compound of formula (I) wherein Q=—CO—, n=1, A=W wherein W is CH₃, X=—S— and B is =—R₃ₐ—ONO₂ wherein R₃ₐ is the group as defined in g) wherein n3' is an integer equal to 4:

(69) A compound of formula (I) wherein Q=—CO—, n=1, A is the group as defined in 1a) wherein R₃ is a straight C₃ alkylene, X=—NH— and B is the group of formula (IA) wherein R₂ is H:

(66)

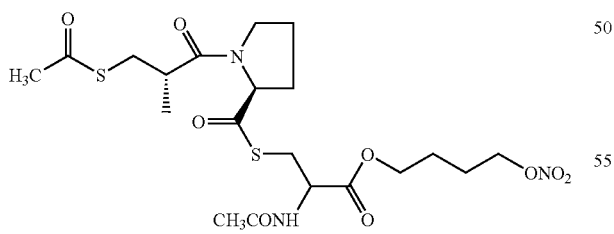

(69)

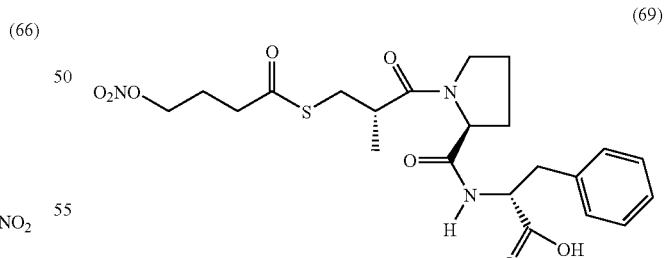

(67) A compound of formula (I) wherein Q=—CO—, n=1, A=W wherein W is CH₃, X=—O— and B is =—R₃ₐ—ONO₂ wherein R₃ₐ is the group as defined in f) wherein n3' is an integer equal to 4:

(70) A compound of formula (I) wherein Q=—CO—, n=1, A is the group as defined in 1a) wherein R₃ is the group as defined in b) wherein n3 is an integer equal to 0 and n3' is an integer equal to 1, X=—NH— and B is the group of formula (IA) wherein R₂ is H:

(70)

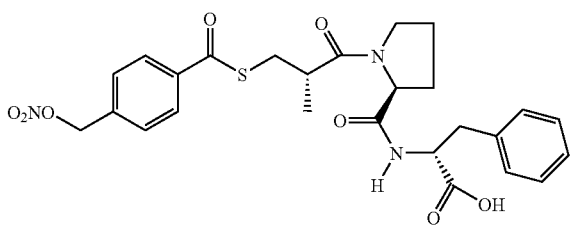

(71) A compound of formula (I) wherein Q=—OCO—, n=1, A is the group as defined in 1a) wherein $R_3$ is a straight $C_4$ alkylene, X=—NH— and B is the group of formula (IA) wherein $R_2$ is H:

(71)

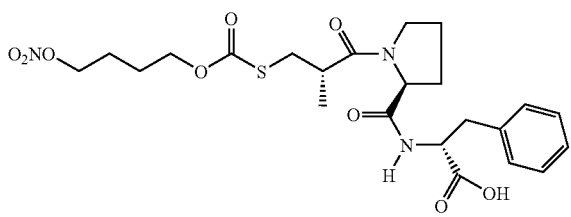

(72) A compound of formula (I) wherein Q=—OCO—, n=1, A is the group as defined in 1a) wherein $R_3$ is a straight $C_3$ alkylene, X=—NH— and B is the group of formula (IA) wherein $R_2$ is H:

(72)

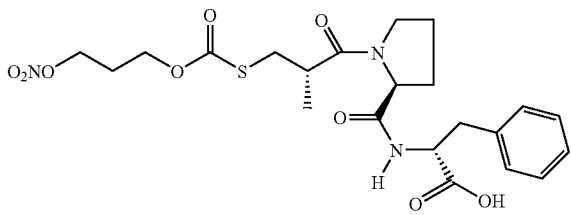

(73) A compound of formula (I) wherein Q=—OCO—, n=1, A is the group as defined in 1a) wherein $R_3$ is the group as defined in b) wherein n3 is an integer equal to 0 and n3' is an integer equal to 1, X=—NH— and B is the group of formula (IA) wherein $R_2$ is H:

(73)

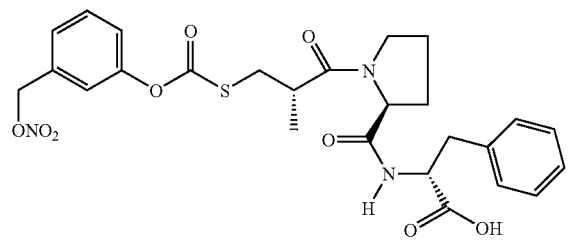

(74) A compound of formula (I) wherein Q=—CO—, n=1, A is the group as defined in 1b) wherein z and Y are H, X=—NH— and B is the group of formula (IA) wherein $R_2$ is H:

(74)

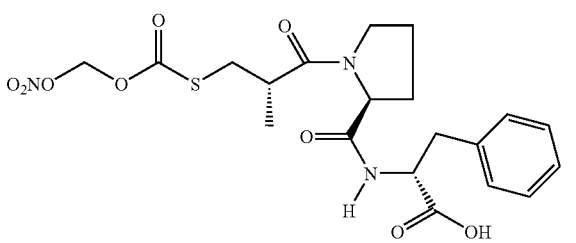

(75) A compound of formula (I) wherein Q=—CO—, n=1, A is the group as defined in 1b) wherein z is H and Y is $CH_3$, X=—NH— and B is the group of formula (IA) wherein $R_2$ is H:

(75)

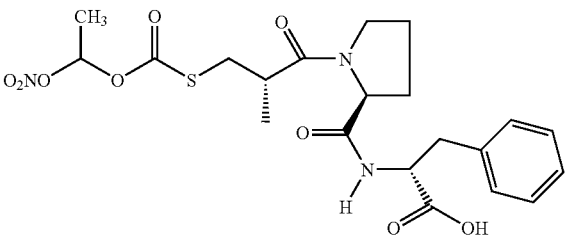

(76) A compound of formula (I) wherein Q=—CO—, n=1, A=W wherein W is $CH_3$, X=—NH— and B is the group of formula (IA) where $R_2$=—$R_{3b}$—$ONO_2$ wherein $R_{3b}$ is a straight $C_3$ alkylene:

(76)

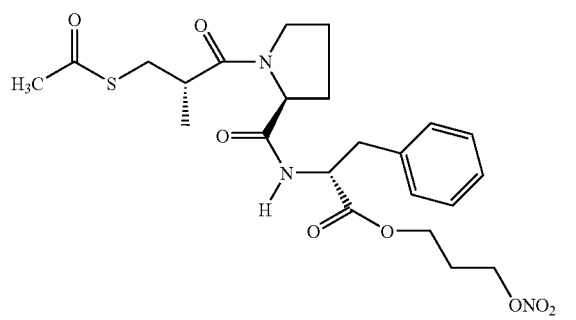

(77) A compound of formula (I) wherein Q=—CO—, n=1, A=W wherein W is $CH_3$, X=—NH— and B is the group of formula (IA) where $R_2$=—$R_{3b}$—$ONO_2$ wherein $R_{3b}$ is a straight $C_4$ alkylene:

(77)

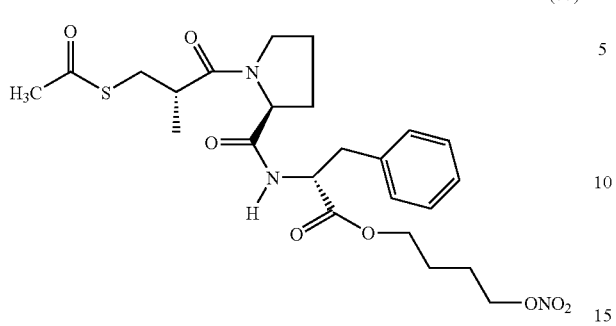

(78) A compound of formula (I) wherein Q=—CO—, n=1, A=W wherein W is CH$_3$, X=—NH— and B is the group of formula (IA) where R$_2$=—R$_{3b}$—ONO$_2$ wherein R$_{3b}$ is the group as defined in b) wherein n3 is an integer equal to 0 and n3' is an integer equal to 1:

(78)

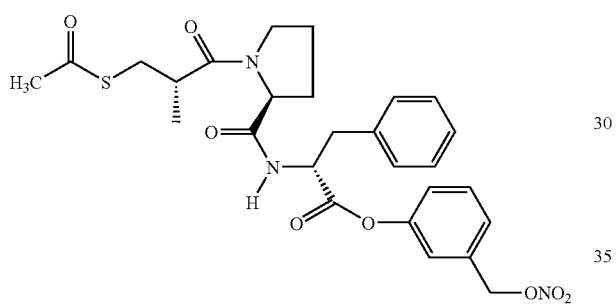

(79) A compound of formula (I) wherein Q=—CO—, n=1, A=W wherein W is CH$_3$, X=—NH— and B is the group of formula (IA) where R$_2$=—R$_{3b}$—ONO$_2$ wherein R$_{3b}$ is the group as defined in b) wherein n3 and n3' are an integer equal to 1:

(79)

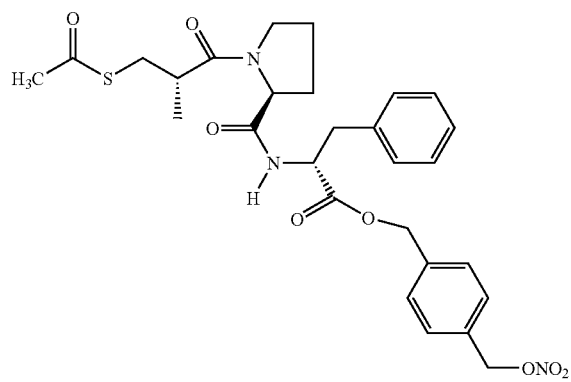

(80). A compound of formula (I) wherein Q=—CO—, n=1, A=W wherein W is CH$_3$, X=—NH— and B is the group of formula (IA) where R$_2$=—R$_{3b}$—ONO$_2$ wherein R$_{3b}$ is a straight C$_5$ alkylene:

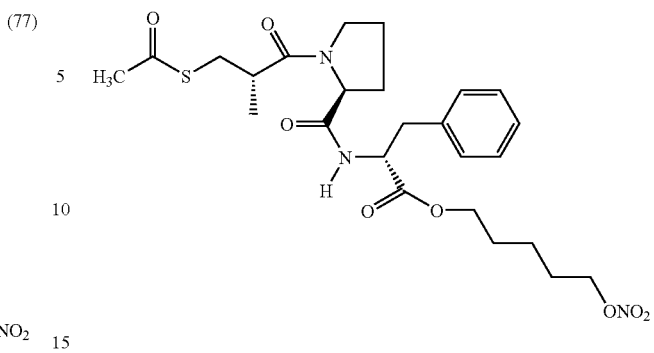

(81). A compound of formula (I) wherein Q=—CO—, n=1, A=W wherein W is CH$_3$, X=—O— and B is =R$_{3a}$—ONO$_2$ wherein R$_{3a}$ is a straight C$_5$ alkylene;

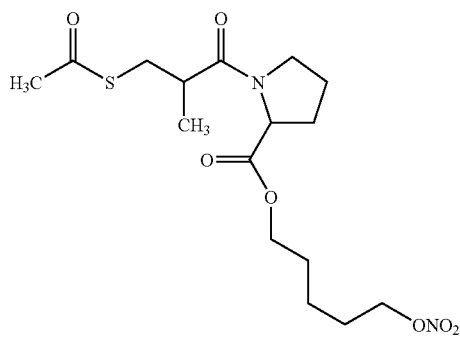

In a further aspect, the present invention provides pharmaceutical compositions which comprise a compound of the general formula (I) reported above in combination with a pharmaceutical acceptable carrier. The daily dose of active ingredient administered to a host can be a single dose or it can be an effective amount divided into several smaller doses that are to be administered throughout the day. Usually, total daily dose may be in amounts from 1 to 2000 mg, preferably from 10 to 1000 mg, in particular from 50 to 500 mg. The dosage regimen and administration frequency for treating the mentioned diseases with the compound of the invention and/or with the pharmaceutical compositions of the present invention will be selected in accordance with a variety of factors, including for example age, body weight, sex and medical condition of the patient as well as severity of the disease, route of administration, pharmacological considerations and eventual concomitant therapy with other drugs. In some instances, dosage levels below or above the aforesaid range and/or more frequent may be adequate, and this logically will be within the judgment of the physician and will depend on the disease state.

The compounds of the invention may be administered orally, parenterally, rectally or topically, by inhalation spray o aerosol, in dosage unit formulations containing conventional non-toxic pharmaceutically acceptable carriers, adjuvants and vehicles as desired. Topical administration may also involve the use of transdermal administration such as transdermal patches or iontophoresis devices. The term "parenteral" as used herein includes subcutaneous injections, intravenous, intramuscular, intrasternal injection or infusion techniques.

Injectable preparations, for example, sterile injectable aqueous or oleaginous suspensions may be formulated according to known art using suitable dispersing or wetting agents and suspending agents. The sterile injectable preparation may also be a sterile injectable solution or suspension in a non-toxic parenterally acceptable diluent o solvent. Among the acceptable vehicles and solvents are water, Ringer's solution and isotonic sodium chloride solution. In addition, sterile, fixed oils are conventionally employed as a solvent or suspending medium. For this purpose any bland fixed oil may be employed including synthetic mono- or diglycerides, in addition fatty acids such as oleic acid find use in the preparation of injectables.

Suppositories for rectal administration of the drug can be prepared by mixing the active ingredient with a suitable non-irritating excipient, such as cocoa butter and polyethylene glycols.

Solid dosage forms for oral administration may include capsules, tablets, pills, powders, granules and gels. In such solid dosage forms, the active compound may be admixed with at least one inert diluent such as sucrose, lactose or starch. Such dosage forms may also comprise, as in normal practice, additional substances other than inert diluents, e.g. lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and the like.

The compounds of the present invention can be synthesized as follows.

Experimentals: Synthesis Procedure

The compound of general formula (I) as above defined, or a pharmaceutically acceptable salt, can be obtained by a process comprising:

i) reacting a compound of formula (II):

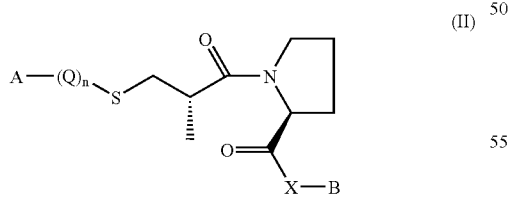

(II)

wherein:

Q and n are as above defined;

A=H, W wherein W is as above defined, aminic protecting group or is chosen from the following groups:

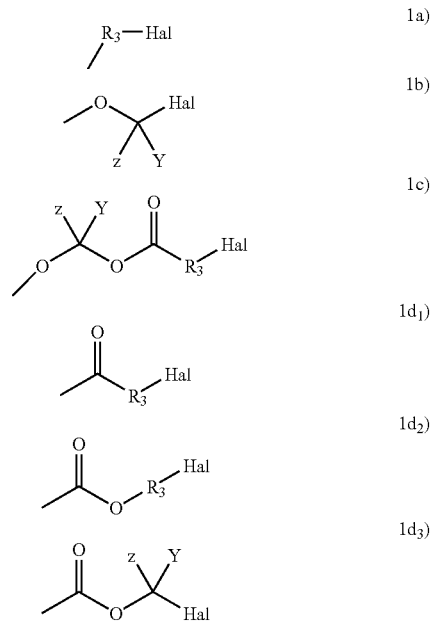

wherein $R_3$, z and Y are as above defined;

X is as above defined;

B=H, carboxylic protecting group, —$R_{3a}$-Hal wherein $R_{3a}$ is as above defined or B is the group of formula (IA) as above defined, wherein $R_2$ is H, a straight or branched ($C_1$–$C_6$)-alkyl or —$R_{3b}$-Hal wherein $R_{3b}$ is as above defined; and Hal is an halogen preferably Cl, Br, and I, with $AgNO_3$ in a suitable organic solvent such as acetonitrile or tetrahydrofuran (THF) under nitrogen at temperatures range between 20°–80° C. and ii) optionally acid hydrolysing the carboxylic protecting group or the aminic protecting group such as tert-butyloxycarbonyl ester (t-Boc), as well known in the art, for example as described in T. W. Greene "Protective groups in organic synthesis", Harvard University Press, 1980 and iii) if desired, converting the resulting compound of general formula (I) into a pharmaceutically acceptable salt thereof.

The compound of formula (II) wherein Q=—CO— or —OCO—, n=1, A=1a), X=—O— or —NH— and B=H, a carboxylic protecting group or the group (IA) wherein $R_2$ is a carboxylic protecting group, having the following formula:

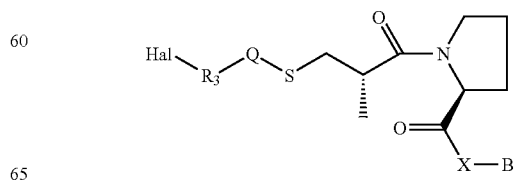

can be obtained reacting a compound of formula (III):

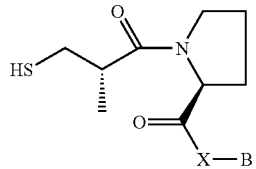
(III)

with a compound of formula (IV):

Hal-R$_3$-Q-Hal  (IV)

wherein Hal, R$_3$ and Q are as above defined;

The reaction is generally carried out in presence of a base in an aprotic polar/non-polar solvent such as THF or CH$_2$Cl$_2$ at temperatures range between 0°–65° C. or in a double phase system H$_2$O/Et$_2$O at temperatures range between 20°–40° C., or when Q=—CO— and X=—O— with the corresponding acid Hal-R$_3$—COOH in presence of a condensing agent like dicyclohexylcarbodiimide (DCC) or N,N'-carbonyldiimidazol (CDI) in solvent such as DMF, THF, chloroform at a temperature in the range from –5° C. to 50° C.

The compound of formula (III) wherein X=—O— and B is H is Captopril and it is commercially available; the compound of formula (III) wherein X=—O— and B is a carboxylic protecting group, preferably ter-butyl, can be obtained from Captopril according to well known reactions as described in U.S. Pat. No. 4,105,776; the compound of formula (III) wherein X=—NH— and B is the group (IA) wherein R$_2$ is a carboxylic protecting group can be obtained as described in U.S. Pat. No. 4,248,883.

The compounds of formula (IV) wherein Q=—CO— are commercially available or can be obtained from the corresponding acids by well known reactions, for example by reaction with thionyl or oxalyl chloride, halides of P$^{III}$ or P$^V$ in solvents inert such as toluene, chloroform, DMF, etc.

The corresponding acids are commercially available compounds.

The compounds of formula (IV) wherein Q=—OCO— are commercially available or can be obtained from the corresponding alcohols by reaction with triphosgene in presence of an organic base.

The compound of formula (II) wherein Q=—CO—, n=1, A=1b), X=—O— and B=H or a carboxylic protecting group, having the following formula:

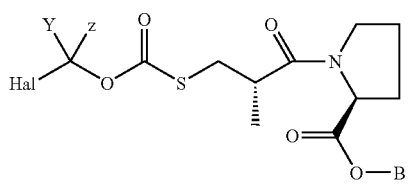

can be obtained reacting a compound of formula (III) as above defined with a compound of formula (V):

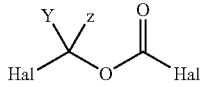
(V)

wherein Hal, Y and z are as above defined;
when Y and z are H or CH$_3$ then the compounds of formula (V) are commercially available;

The reaction is generally carried out in presence of a base in an aprotic polar solvent such as THF or dioxane at room temperature.

Alternatively, the compound of general formula (I) wherein Q=—CO—, n=1, A=1c), X=—O— and B=H or a carboxylic protecting group, having the following formula:

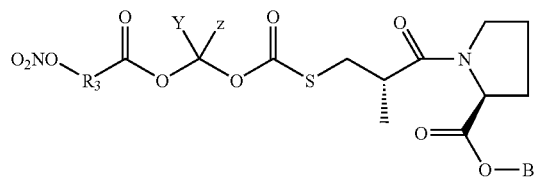

can be obtained by reacting a compound of formula (II) wherein Q=—CO—, n=1, A=1b), X=—O— and B=H or a carboxylic protecting group, as above described, having the following formula:

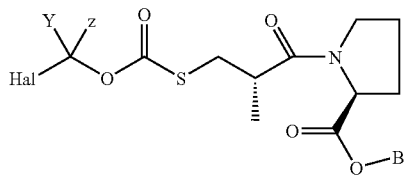

wherein Hal, Y and z are as above defined;

with a compound of formula (VI):

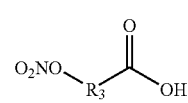
(VI)

wherein R$_3$ is as above defined;

The reaction is generally carried out in presence of a base in an aprotic polar solvent such as THF at room temperature, or using the preformed Cs salt of the acid.

The compounds of formula (VI) can be obtained from the corresponding alcohols by reaction with nitric acid and acetic anhydride in a temperature range from –50° C. to 0° C.

The compound of formula (II) wherein Q=—COCH(R)NH—, n=1, A=1d$_{1-3}$), X=—O— and B=H or a carboxylic protecting group, having the following formula:

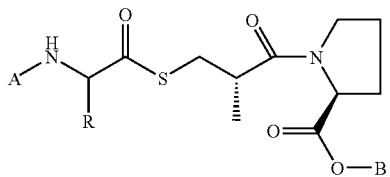

can be obtained by reacting a compound of formula (VII):

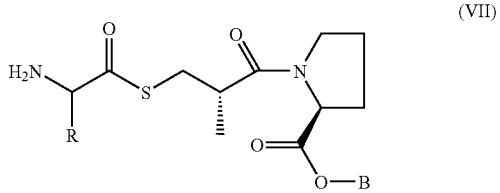

(VII)

with a compound of formula (IV) as above defined wherein Q=—CO—, when A=1d$_1$; or
with a compound of formula (IV) as above defined wherein Q=—OCO—, when A=1d$_2$; or
with a compound of formula (V) as above defined, when A=1d$_3$;

The reaction is generally carried out in presence of an organic or inorganic base in a dioxane/H$_2$O solution or in an organic solvent such as CH$_2$Cl$_2$ at temperatures range between 0°–40° C.

The compound of formula (VII) can be obtained hydrolysing a compound of formula (VIII) as known in the literature, for example as described in T. W. Greene "Protective groups in organic synthesis", Harvard University Press, 1980:

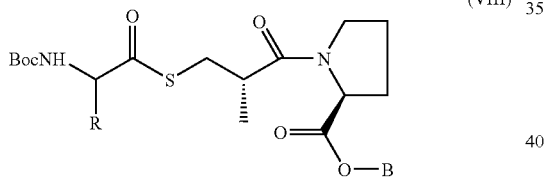

(VIII)

The compounds of formula (VIII) can be obtained reacting a compound of formula (III), as above defined, with an N-BOC aminoacid and carbonyldiimidazole in THF at temperatures range between 0°–40° C.

The reaction is generally carried out in a monophasic or biphasic system in presence of an organic or inorganic base.

The compound of formula (II) wherein Q is as above defined, n=1, A=H, W, 1a), X=—O— and B is —R$_{3a}$-Hal can be obtained by esterifying a compound of formula (II) wherein:

Q is as above defined, n=1, A=H, W, 1a), X=—O— and B is H with a compound of formula (IX):

HO—R$_{3a}$-Hal        (IX)

wherein Hal and R$_{3a}$ are as above defined;

The reaction is generally carried out in presence of condensing agent such as DCC, in solvent such as CHCl$_3$/EtOAc.

The compounds of formula (IX) are commercially available.

Alternatively the compound of general formula (I) wherein Q=—CO— or —COCH(R)NH—, A=W or H, n=1, X=—O— and B is —R$_{3a}$-Hal can be obtained by esterifying a compound of formula (II) wherein:

Q=—CO— or —COCH(R)NH—, A=W or H, n=1, X=—O— and B is H with a compound of formula (X):

HO—R$_{3a}$—ONO$_2$        (X)

wherein R and R$_{3a}$ are as above defined;

The reaction is generally carried out in presence of condensing agent as above reported.

The compounds of formula (X) can be obtained reacting a compound of formula (IX) with AgNO$_3$ in a suitable organic solvent such as acetonitrile or THF under nitrogen at temperatures range between 20°–80° C.

The compound of formula (II) wherein Q=—CO—, n=1, A=W, X=—O— or —S— and B is —R$_{3a}$-Hal with R$_{3a}$=f) or g) can be obtained by esterifying a compound of formula (II) wherein:

Q=—CO—, n=1, A=W, X=—O— and B is H with a compound of formula (XI) when R$_{3a}$=f):

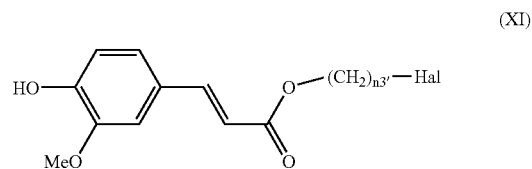

(XI)

or with a compound of formula (XII) when R$_{3a}$=g)

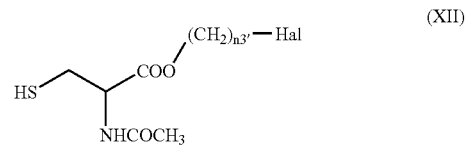

(XII)

wherein n3', R$_{3a}$, W, f) and g) are as above defined;

The reaction is generally carried out in presence of condensing agent such as DCC or CDI, in solvent such as DMF, THF, chloroform at a temperature in the range from −5° C. to 50° C.

The compounds of formula (XI) and (XII) wherein n3' is an integer equal to 4, can be obtained from the corresponding acids by reaction with triphenylphosphine in the presence of an halogenating agent such as CBr$_4$ in THF at room temperature.

The compound of formula (II) wherein Q=—CO—, n=1, A=W, X=—NH— and B=(IA) with R$_2$=—R$_{3b}$-Hal, having the following formula:

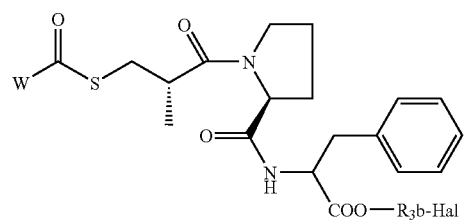

can be obtained by reacting a compound of formula (XIII):

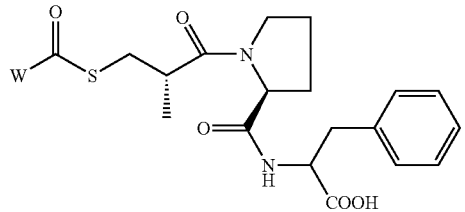

(XIII)

with a compound of formula (XIV):

HO—R$_{3b}$-Hal (XIV)

wherein Hal, W, (IA) and R$_{3b}$ are as above defined;

The reaction is generally carried out in presence of condensing agent such as DCC, in solvent such as CHCl$_3$.

The compounds of formula (XIII) can be obtained by known methods from the compounds of formula (XV) by acid hydrolysis, as described in U.S. Pat. No. 4,248,883

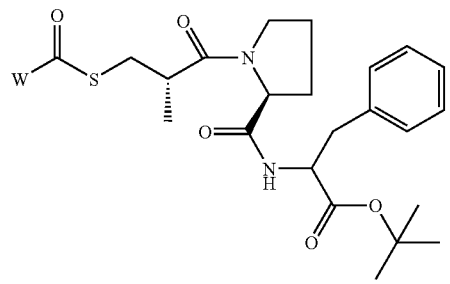

(XV)

When in formula (XIII) W is CH$_3$, the compound is known as Alacepril.

The compounds of formula (XIV) are commercially available. The following examples are offered to further illustrate, but not to limit, the claimed invention.

EXAMPLE 1

Synthesis of 1-[(2S)-3-(4-Nitrooxymethylbenzoyl) mercapto-2-methyl-1-oxopropyl]-L-proline (corresponding to compound 3)

α-chloro-toluic acid (9.0 g, 0.0528 Mol) and carbonyldiimidazole (10.3 g, 0.0634 Mol) were dissolved in THF (100 ml) and stirred overnight at room temperature. Then TEA was added (7.4 ml. 0.0528 Mol) and to this reaction mixture a solution of captopril (11.5 g, 0.0528 Mol) in THF (20 ml) was added dropwise and the reaction was stirred overnight at room temperature. The mixture was then partitioned between KHSO4 10% and EtOAc (120 ml). The organic layer was separated and the aqueous phase was extracted with EtOAc (2×60 ml). The combined organic phases were washed with water (3×60 ml), dried over sodium sulphate and evaporated under reduced pressure affording 14.1 g of 1-[(2S)-3-(4-chloromethylbenzoyl)mercapto-2-methyl-1-oxopropyl]-L-proline as a white solid used for the next step without further purification.

1-[(2S)-3-(4-chloromethylbenzoyl)mercapto-2-methyl-1-oxopropyl]-L-proline (13.94 g, 0.0378 Mol) was dissolved in acetonitrile (150 ml) under nitrogen in the dark. Silver nitrate (12.83 g, 0.0756 Mol) was added and the mixture was heated to 60° C. for 6 h. After cooling silver salts were filtered off and the mixture was diluted with CH$_2$Cl$_2$ (150 ml) and washed with water (3×100 ml), then with brine (3×100 ml). The organic layer was then evaporated under reduced pressure affording the title compound (8.90 g, 60%) as a dense pale yellow oil.

$^1$H-NMR: (CDCl$_3$) (2 rotamers) 8.24 (d, 2H), 7.54 (d, 2H), 5.52 (s, 2H), 4.63 (m, 1H), 3.59 (m, 2H), 3.13 (m, 1H), 2.96 (m, 2H), 2.51 (m, 1H), 2.09 (m, 1H), 1.87 (m, 2H), 1.28 (d, 3H).

C$_{17}$H$_{20}$N$_2$O$_7$S: required % (found %) C 51.51 (51.41) H 5.09 (5.15) N 7.07 (7.05).

EXAMPLES 1a, 1b

With the same procedure as described in Example 1, but starting utilizing the appropriate ω-alogeno substituted-carboxylic acid the following compounds can be obtained:

Ex. 1a). 1-[(2S)-3-(4-Nitrooxybutanoyl)mercapto-2-methyl-1-oxopropyl]-L-proline (corresponding to compound 1)(oil, 48%).

$^1$H-NMR: (CDCl$_3$) (2 rotamers)), 4.63 (bd, 1H), 4.49 (t, 2H), 3.59 (m, 2H), 3.13 (m, 1H), 2.96 (m, 2H), 2.51 (m, 1H) 2.10 (m, 3H), 1.87 (m, 4H), 1.27 (d, 3H).

C$_{13}$H$_{20}$N$_2$O$_7$S: required % (found %) C 44.82 (44.75) H 5.79 (5.90) N 8.04 (7.95).

Ex. 1b). 1-[(2S)-3-(4-Nitrooxypentanoyl)mercapto-2-methyl-1-oxopropyl]-L-proline (corresponding to compound 2)(oil, 50%).

$^1$H-NMR: (CDCl$_3$) (2 rotamers)), 4.63 (m, 1H), 4.49 (t, 2H), 3.59 (m, 2H), 3.13 (m, 1H), 2.95 (m, 2H), 2.51 (m, 1H), 2.10 (m, 3H), 1.87 (m, 6H), 1.28 (d, 3H).

EXAMPLE 2

Synthesis of 1-[(2S)-3-(4-Nitrooxybutoxycarbonyl) mercapto-2-methyl-1-oxopropyl]-L-proline (corresponding to compound 4)

Captopril (3.50 g, 0.0161 Mol) and N,N-diisopropyl ethylamine (6.80 ml, 0.039 Mol) were dissolved in H$_2$O/CH$_3$CN (80 ml, 1:1) and the mixture was cooled to 0° C. Then 4-chlorobutylchloroformate (2.70 ml, 0.0198 Mol) was added and the reaction was slowly warmed to room temperature and stirred for 4 h. The mixture was then partitioned between HCl (4%, 100 ml) and EtOAc (100 ml). The organic layer was separated and the aqueous phase was extracted with EtOAc (2×100 ml). The combined organic phases were washed with brine (3×60 ml), dried over sodium sulphate and evaporated under reduced pressure affording 1-[(2S)-3-(4-chlorobutoxycarbonyl)mercapto-2-methyl-1-oxopropyl]-L-proline (5.90 g) as a colourless oil that was used without further purification.

1-[(2S)-3-(4-chlorobutoxycarbonyl)mercapto-2-methyl-1-oxopropyl]-L-proline (5.80 g, 0.0157 Mol) was dissolved in CH$_3$CN (100 ml) and NaI (23.9 g, 0.160 Mol) was added to the solution. The mixture was refluxed for 7 h, then concentrated and diluted with CH$_2$Cl$_2$. The solid formed was filtered off and the organic phase was washed with H$_2$O (3×50 ml), dried over sodium sulphate and evaporated under reduced pressure affording 1-[(2S)-3-(4-iodobutoxycarbonyl) mercapto-2-methyl-1-oxopropyl]-L-proline (7.10 g) as an oil that was used without further purification.

1-[(2S)-3-(4-iodobutoxycarbonyl)mercapto-2-methyl-1-oxopropyl]-L-proline (7.0 g, 0.0152 Mol) was dissolved in CH₃CN (40 ml) under nitrogen, in the dark, and AgNO₃ (8.44 g, 0.497 Mol) was added. The mixture was heated at 40–50° C. for 2 hours. The salts were filtered off, the solution was diluted with CH₂Cl₂ and the organic phase was washed with H₂O (2×50 ml) and brine (50 ml), dried over sodium sulphate and evaporated under reduced pressure affording the title compound as a pure yellow oil (5.13 g, 89%).

¹H-NMR: (CDCl₃) (2 rotamers) 4.65 (m, 1H), 4.50 (t, 2H), 4.28 (t, 2H), 3.61 (m, 2H), 3.12 (m, 1H), 2.96 (m, 2H), 2.50 (m, 1H), 2.14 (m, 3H), 1.83 (m, 4H), 1.28 (d, 3H).

EXAMPLES 2a, 2b

With the same procedure as described in Example 2, but starting utilizing the appropriate ω-alogeno-substituted-chloroformiate the following compounds can be obtained:

Ex. 2a). 1-[(2S)-3-(4-Nitrooxypropoxycarbonyl)mercapto-2-methyl-1-oxopropyl]-L-proline (corresponding to compound 5) (oil 75%).

¹H-NMR: (CDCl₃) (2 rotamers) 4.65 (m, 1H), 4.50 (t, 2H), 4.28 (t, 2H), 3.61 (m, 2H), 3.12 (m, 1H), 2.96 (m, 2H), 2.50 (m, 1H), 2.14 (m, 3H), 1.83 (m, 2H), 1.28 (d, 3H).

Ex. 2b). 1-[(2S)-3-(3-Nitrooxymethylbenzoyl)mercapto-2-methyl-1-oxopropyl]-L-proline (corresponding to compound 6) (foam 75%).

¹H-NMR: (CDCl₃) (2 rotamers) 7.47–7.13 (4H, m), 5.44 (2H, s), 4.65 (m, 1H), 3.61 (m, 2H), 3.12 (m, 1H), 2.96 (m, 2H), 2.50 (m, 1H), 2.14 (m, 1H), 1.83 (m, 2H), 1.28 (d, 3H).

EXAMPLE 3

Synthesis of 1-[(2S)-3-(Nitrooxymethoxycarbonyl) mercapto-2-methyl-1-oxopropyl]-L-proline (corresponding to compound 8)

Captopril (2.48 g, 0.0114 Mol) and N,N-diisopropyl ethylamine (4.50 ml, 0.0258 Mol) were dissolved in dioxane/H₂O (30 ml, 1:1). The mixture was cooled to 0° C. and 1-chloromethyl chloroformate (1.20 ml, 0.0147 Mol) was added. The reaction was stirred at 0° C. for 4 h, then partitioned between HCl (4%, 30 ml) and CH₂Cl₂ (30 ml). The aqueous phase was extracted with CH₂Cl₂ (2×30 ml) and the combined organic phases were washed with HCl (4%, 30 ml) and brine (3×30 ml), dried over sodium sulphate and evaporated under reduced pressure affording 1-[(2S)-3-(chloromethoxycarbonyl)mercapto-2-methyl-1-oxopropyl]-L-proline as a clear oil (2.60 g) that was used without further purification.

1-[(2S)-3-(chloromethoxycarbonyl)mercapto-2-methyl-1-oxopropyl]-L-proline (2.59 g, 0.0084 Mol) was dissolved in dry CH₃CN (18 ml) under nitrogen, in the dark, and AgNO₃ (3.20 g, 0.019 Mol) was added. The mixture was heated at 40–50° C. for 5 h and the salts were filtered off. It was then diluted with CH₂Cl₂ and the organic phase was washed with H₂O (2×50 ml) and brine (3×100 ml), dried over sodium sulphate and evaporated under reduced pressure affording the title compound as a pure light yellow foam (2.26 g, 84%).

¹H-NMR: (CDCl₃) (2 rotamers) 6.1 (dd, 2H), 4.51 (m, 1H), 3.64 (m, 2H), 3.17 (m, 1H), 2.99 (m, 2H), 2.35 (m, 1H), 2.08 (m, 3H), 1.29 (d, 3H).

EXAMPLE 3a

With the same procedure as described in Example 3, but starting from 1-chloroethychloroformiate, 1-[(2S)-3-(1-Nitrooxyethoxycarbonyl)mercapto-2-methyl-1-oxopropyl]-L-proline (corresponding to compound 7) was obtained as an oil (35%).

¹H-NMR: (CDCl₃) (2 rotamers) 6.5 (q, 1H), 4.51 (m, 1H), 3.64 (m, 2H), 3.17 (m, 1H), 2.99 (m, 2H), 2.35 (m, 1H), 2.08 (m, 3H), 1.98 (d, 3H), 1.29 (d, 3H).

EXAMPLE 4

Synthesis of L-alanyl-(2S)-3-mercapto-2-methylpropanoyl-L-proline 3-nitrooxypropyl ester hydrochloride (corresponding to compound 39)

N-Boc alanine (10 g, 0.0528 Mol) and carbonyldiimidazole (10.3 g, 0.0634 Mol) were dissolved in THF (100 ml) and stirred overnight at room temperature. Then TEA was added (7.4 ml. 0.0528 Mol) and to this reaction mixture a solution of captopril (11.5 g, 0.0528 Mol) in THF (20 ml) was added dropwise and the reaction was stirred overnight at room temperature. The mixture was then partitioned between KHSO4 10% and EtOAc (120 ml). The organic layer was separated and the aqueous phase was extracted with EtOAc (2×60 ml). The combined organic phases were washed with water (3×60 ml), dried over sodium sulphate and evaporated under reduced pressure affording 16 g of L-N-Boc-alanyl-(2S)-3-mercapto-2-methylpropanoyl-L-proline as a white solid.

¹H-NMR (CDCl₃): (2 rotamers) 5.05 (bd, 1H), 4.90 (bd, 1H), 4.60 (m, 1H), 4.45 (m, 1H), 4.30 (m, 1H), 3.55 (m, 2H), 3.1 and 2.9 (m, 3H), 2.5 (m, 1H), 2.05 (m, 3H), 1.47 (s, 9H) 1.4 (d, 3H), 1.25 (d, 3H).

To a cold (0° C.) solution of L-N-Boc-alanyl-(2S)-3-mercapto-2-methylpropanoyl-L-proline (9.6 g, 0.0236 Mol), bromopropanol (1.71 ml, 0.0196 Mol) and DMAP (0.24 g, 0.00196 Mol) in CHCl₃ (100 ml) a solution of DCC (4.87 g, 0.0236 Mol) in CHCl₃ (20 ml) was added dropwise and the reaction was slowly warmed to room temperature and stirred overnight. Then the solvent was evaporated under reduced pressure and the mixture was dissolved in EtOAc. The precipitated DCU was filtered off. The solution was evaporated and the residue was dissolved in EtOAc/n-Hexane 1:1 (100 ml) and again the precipitated DCU was filtered off. The solution was evaporated and the residue was purified by flash chromatography (Hexane: EtOAc 6.5:3.5) to afford 7 g of L-N-boc alanyl-(2S)-3-mercapto-2-methylpropanoyl-L-proline 3-bromopropyl ester as a white foam.

¹H-NMR: (CDCl₃) (2 rotamers) 5.05 (bd, 1H), 4.4 (m, 1H), 4.25 and 4.2 (m, 3H), 3.55 (t, 2H), 3.4 (t, 2H), 3.0 and 2.9 (m, 2H), 2.75 (m, 1H), 2.15 (m, 3H), 1.95 (m, 3H), 1.4 (s, 9H), 1.3 (d, 3H), 1.2 (d, 3H).

L-N-boc-alanyl-(2S)-3-mercapto-2-methylpropanoyl-L-proline 3-bromopropyl ester (7.0 g, 0.0132 Mol) was dissolved in dry CH₃CN (100 ml) under nitrogen, in the dark, and AgNO₃ (6.7 g, 0.0396 Mol) was added. The mixture was heated at 60° C. for 8 h. Then the salts were filtered off and the residue was diluted with CH₂Cl₂ and the organic phase was washed with H₂O (2×50 ml) and brine (3×100 ml), dried over sodium sulphate and evaporated under reduced pressure. The residue was purified by flash chromatography (n-hexane/EtOAc 1:1) affording 3 g of L-N-boc-alanyl-(2S)-3-mercapto-2-methylpropanoyl-L-proline 3-nitrooxyopropyl ester as a white solid.

¹H-NMR (CDCl₃): (2 rotamers) 4.9 (bd, 1H), 4.56 (t, 2H) 4.47 (m, 1H), 4.35 and 4.25 (m, 3H), 3.63 (t, 2H), 3.05 and 2.97 (m, 2H), 2.85 (m, 1H), 2.23 and 2.18 (m, 6H), 1.47 (s, 9H), 1.37 (d, 3H), 1.25 (d, 3H).

In a cold (0° C.) solution of L-N-boc-alanyl-(2S)-3-mercapto-2-methylpropanoyl-L-proline 3-nitrooxypropyl ester (3.0 g, 0.0058 Mol) in EtOAc (30 ml) a gaseous HCl stream was passed. After 1 hour the solution was evaporated and the residue was crystallized from EtoAc/diethyl ether affording the title compound (2.5 g 95%) as a white solid.

¹H-NMR (CDCl₃): (2 rotamers) 8.69 (bs, 3H), 4.6 and 4.5 (m, 3H), 4.35 (ds, 1H), 4.19 (t, 2H), 3.55 (bm, 2H), 3.15 (m, 2H), 2.85 (m, 1H), 2.2 and 2.0 (m, 6H), 1.7 (d, 3H) 1.25 (d, 3H).

EXAMPLES 4a, 4b, 4c

Ex. 4a). With the same procedure as described in Example 4 but utilizing 4-bromopropanol L-Alanyl-(2S)-3-mercapto-2-methylpropanoyl-L-proline 4-nitrooxybutyl ester hydrochloride (corresponding to compound 38) was obtained as a white solid (80%);

Ex. 4b). With the same procedure as described in Example 4 but utilizing 3-bromomethylphenol L-Alanyl-(2S)-3-mercapto-2-methylpropanoyl-L-proline 3-nitrooxymethylphenyl ester hydrochloride (corresponding to compound 40) was obtained as a white solid (80%);

Ex. 4c). With the same procedure as described in Example 4 but utilizing 4-bromomethylbenzylalcohol L-Alanyl-(2S)-3-mercapto-2-methylpropanoyl-L-proline 4-nitrooxymethylbenzyl ester hydrochloride (corresponding to compound 41) was obtained as a white solid (78%).

EXAMPLE 5

Synthesis of 1-[3-(4-Nitrooxybutoxycarbonyl)-L-alanyl-(2S)-mercapto-2-methyl-1-oxopropyl]-L-proline (corresponding to compound 16)

In a cold (0° C.) solution of L-N-Boc-alanyl-(2S)-3-mercapto-2-methylpropanoyl-L-proline (12 g, 0.015 Mol), (obtained as described in first step of Example 4) in EtOAc (50 ml) a gaseous HCl stream was passed. After 1 h the solution was evaporated and the residue was crystallized from EtOAc/diethyl ether affording L-alanyl-(2S)-3-mercapto-2-methylpropanoyl-L-proline hydrochloride (8.0 g 90%) as a white solid.

L-alanyl-(2S)-3-mercapto-2-methylpropanoyl-L-proline hydrochloride (4.6 g, 0.0161 Mol) and N,N-diisopropyl ethylamine (6.80 ml, 0.039 Mol) were dissolved in H₂O/CH₃CN (80 ml, 1:1) and the mixture was cooled to 0° C. Then 4-chlorobutylchloroformate (2.70 ml, 0.0198 Mol) was added and the reaction was slowly warmed to room temperature and stirred for 4 h. The mixture was then partitioned between HCl (4%, 100 ml) and EtOAc (100 ml). The organic layer was separated and the aqueous phase was extracted with EtOAc (2×100 ml). The combined organic phases were washed with brine (3×60 ml), dried over sodium sulphate and evaporated under reduced pressure affording 1-[(4-chlorobutoxycarbonyl)-L-alanyl-(2S)-3-mercapto-2-methyl-1-oxopropyl]-L-proline (5.17 g) as a foam that was used without further purification.

1-[(4-chlorobutoxycarbonyl)-L-alanyl-(2S)-3-mercapto-2-methyl-1-oxopropyl]-L-proline (3.15 g, 0.0078 Mol) was dissolved in CH₃CN (100 ml) and NaI (11.7 g, 0.078 Mol) was added to the solution. The mixture was refluxed for 7 h, then concentrated and diluted with CH₂Cl₂. The solid formed was filtered off and the organic phase was washed with H₂O (3×50 ml), dried over sodium sulphate and evaporated under reduced pressure affording 1-[(4-iodobutoxycarbonyl)-L-alanyl-(2S)-3-mercapto-2-methyl-1-oxopropyl]-L-proline (4.03 g) as a foam that was used without further purification.

1-[(4-iodobutoxycarbonyl)-L-alanyl-(2S)-3-mercapto-2-methyl-1-oxopropyl]-L-proline (4.0 g, 0.0078 Mol) was dissolved in CH₃CN (40 ml) under nitrogen, in the dark, and AgNO₃ (2.6 g, 0.0156 Mol) was added. The mixture was heated at 40–50° C. for 2 h. The salts were filtered off, the solution was diluted with CH₂Cl₂ and the organic phase was washed with H₂O (2×50 ml) and brine (50 ml), dried over sodium sulphate and evaporated under reduced pressure affording the title compound as a pure yellow oil (3.6 g, 90%).

EXAMPLES 5a, 5b, 5c, 5d

With the same procedure as described in Example 5, but starting utilizing the appropriate ω-alogeno substituted-chloroformiate the following compounds can be obtained:

Ex. 5a). 1-[3-(4-Nitrooxypropoxycarbonyl)-L-alanyl-(2S)-mercapto-2-methyl-1-oxopropyl]-L-proline (corresponding to compound 17);

Ex. 5b).1-[3-(Nitrooxymethylphenoxycarbonyl)-L-alanyl-(2S)-mercapto-2-methyl-1-oxopropyl]-L-proline (corresponding to compound 24).

EXAMPLES. 5c) 5d)

Using chloromethylchloroformiate or 1-chloroethylchloroformiate but directing nitrating the intermediate compounds (as described in Example 3) the following compounds can be obtained:

Ex. 5c) 1-[3-(Nitrooxymethoxycarbonyl)-L-alanyl-(2S)-mercapto to-2-methyl-1-oxopropyl]-L-proline (corresponding to compound 19) (oil, 60%);

Ex. 5d). 1-[3-(1-Nitrooxyethoxycarbonyl)-L-alanyl-(2S)-mercapto-2-methyl-1-oxopropyl]-L-proline (corresponding to compound 18) (oil, 65%).

EXAMPLE 6

Synthesis of 1-[3-(4-Nitrooxymethylbenzoyl)-L-alanyl-(2S)-mercapto-2-methyl-1-oxopropyl]-L-proline (corresponding to compound 14)

α-chloro-toluic acid (9.0 g, 0.0528 Mol) and carbonyldiimidazole (10.3 g, 0.0634 Mol) were dissolved in THF (100 ml) and stirred overnight at room temperature. Then TEA was added (7.4 ml. 0.0528 Mol) and to this reaction mixture a solution of L-alanyl-(2S)-3-mercapto-2-methylpropanoyl-L-proline hydrochloride (15.2 g, 0.0528 Mol) (obtained as described in first step Example 5) in THF (30 ml) was added dropwise and the reaction was stirred overnight at room temperature. The mixture was then partitioned between KHSO4 10% and EtOAc (120 ml). The organic layer was separated and the aqueous phase was extracted with EtOAc (2×60 ml). The combined organic phases were washed with water (3×60 ml), dried over sodium sulphate and evaporated under reduced pressure affording 17.6 g. of 1-[3-(4-chloromethylbenzoyl)-L-alanyl-(2S)-mercapto-2-methyl-1-oxopropyl]-L-proline as a white solid used for the next step without further purification.

1-[3-(4-chloromethylbenzoyl)-L-alanyl-(2S)-mercapto-2-methyl-1-oxopropyl]-L-proline (16.6 g, 0.0378 Mol) was dissolved in acetonitrile (150 ml) under nitrogen in the dark. Silver nitrate (12.83 g, 0.0756 Mol) was added and the mixture was heated to 60° C. for 6 h. After cooling silver salts were filtered off and the mixture was diluted with $CH_2Cl_2$ (150 ml) and washed with water (3×100 ml), then with brine (3×100 ml). The organic layer was then evaporated under reduced pressure affording the title compound (10.6 g, 60%) as a pale yellow foam.

EXAMPLES 6a, 6b

With the same procedure as described in Example 6, but starting utilizing the appropriate ω-alogeno substituted-carboxylic acid the following compounds can be obtained:

Ex. 6a). 1-[3-(4-nitrooxypentanoyl)-L-alanyl-(2S)-mercapto-2-methyl-1-oxopropyl]-L-proline (corresponding to compound 10);

Ex. 6b). 1-[3-(4-nitrooxybutanoyl)-L-alanyl-(2S)-mercapto-2-methyl-1-oxopropyl]-L-proline (corresponding to compound 11).

EXAMPLE 7

With the same procedure described in Example 4, N-Boc-glycine (9.25 g) (instead of N-Boc-alanine) was connected to captopril affording N-Boc-glycyl-(2S)-3-mercapto-2-methylpropanoyl-L-proline (14.5 g). By acid hydrolysis as described in Example 5, glycyl-(2S)-3-mercapto-2-methyl-propanoyl-L-proline hydrochloride (7.5 g) can be obtained. From it and the appropriate ω-alogeno substituted-chloroformiate or ω-bromo substituted-carboxylic acid the compounds 12, 13, 15, 20, 21, 22, 23, 25 can be obtained.

EXAMPLE 8

Synthesis of 1-[3-(Acetylthio)-(2S)-methyl-1-oxopropyl]-L-proline 3-nitrooxypropyl ester (corresponding to compound 59)

A solution of DCC (2.37 g, 0.0115 Mol) in chloroform (20 ml) was dropped into a cold solution (0° C.) of N-[3-(acetylthio)-(2S)-methyl-1-oxopropyl]-L-proline hydrate (3.0 g, 0.0115 Mol), 3-bromopropanol (0.84 ml, 0.0096 Mol) and DMAP (0.142 g, 0.0011 mol) in chloroform (60 ml). The cold bath was removed and the mixture was stirred overnight. Then the solvent was evaporated under reduced pressure and the mixture was dissolved in EtOAc. The precipitated DCU was filtered off and the residue was purified by flash chromatography (Hexane: EtOAc 7:3) to afford 1-[3-(acetylthio)-(2S)-methyl-1-oxopropyl]-L-proline 3-bromopropyl ester (3.30 g) as a colourless oil.

1-[3-(acetylthio)-(2S)-methyl-1-oxopropyl]-L-proline 3-bromopropyl ester (3.0 g, 0.0079 Mol) was dissolved in acetonitrile (50 ml) under nitrogen in the dark. Silver nitrate (4.03 g, 0.0237 Mol) was added and the mixture was heated to 60° C. for 6 h. After cooling silver salts were filtered off and the mixture was diluted with $CH_2Cl_2$ (100 ml) and washed with water (3×100 ml) then with brine (3×60 ml). The organic layer was then evaporated under reduced pressure and the residue was purified by flash chromatography (Hexane: EtOAc 6:4) to afford the title compound (1.70 g, 48%) as a colourless oil.

$^1$H-NMR (CDCl$_3$): (2 rotamers) 4.57 (t, 2H), 4.48 (m, 1H), 4.25 (2H, m), 3.62 (2H, t), 3.10 (1H, dd), 2.98 (1H, dd), 2.82 and 2.55 (1H, m), 2.34 and 2.31 (s, 3H), 2.3–1.9 (6H, m) 1.24 and 1.19 (3H, d).

EXAMPLES 8a, 8b

Ex. 8a). With the same procedure described in Example 8 but utilizing 4-bromopropanol 1-[(2S)-3-(Acetylthio)-2-methyl-1-oxopropyl]-L-proline 4-nitrooxybutylester (corresponding to compound 58) was obtained as a colourless oil (50%).

$^1$H-NMR (CDCl$_3$) (2 rotamers) 4.58 (t, 2H), 4.48 (m, 1H) 4.25 (2H, m), 3.62 (2H, t), 3.10 (1H, dd), 2.98 (1H, dd), 2.82 and 2.55 (1H, m), 2.34 and 2.31 (s, 3H), 2.3–1.8 (8H, m) 1.24 and 1.19 (3H, d).

Ex. 8b). With the same procedure described in Example 8 but utilizing 3-bromomethylphenol 1-[3-(acetylthio)-(2S)-methyl-1-oxopropyl]-L-proline 3-nitrooxymethylphenyl ester (corresponding to compound 60) was obtained as a dense pale yellow oil (55%).

$^1$H-NMR (CDCl$_3$): (2 rotamers) 7.5–7.1 (4H,m), 5.46 and 5.43 (2H, s), 4.75–4.6 (1H,m), 3.7 (2H,m), 3.10 (1H, dd), 2.98 (1H, dd), 2.85 (1H, m), 2.48–2.0 (4H, m), 1.23 (3H, d).

EXAMPLE 9

Synthesis of 1-[(2S)-3-(Acetylthio)-2-methyl-1-oxopropyl]-L-prolyl-L-phenylalanine 3-nitrooxymethyl phenyl ester (i.e. Alacepril 3-nitrooxymethyl phenyl ester) (corresponding to compound 78)

N-[3-(acetylthio)-(2S)-methyl-1-oxopropyl]-L-proline hydrate (1.00 g, 0.039 Mol), 4-dimethylaminopyridine (0.095 g, 0.008 Mol), L-Phenylalanine tert-butyl ester (1.00 g, 0.039 Mol) and triethylamine (1.60 ml, 0.12 Mol) were dissolved in CHCl$_3$ (15.0 ml). The solution was cooled to 0° C. and N'-(3-Dimethylaminopropyl)-N-ethylcarbodiimide hydrochloride (0.890 mg, 0.046 Mol) was added. The reaction was stirred at room temperature for 6 h then it was diluted with CH$_2$Cl$_2$ (15 ml) and extracted with HCl 4%, (3×20 ml), NaHCO$_3$ 5%, (3×20 ml), washed with brine (3×20 ml), dried over Na$_2$SO$_4$ and evaporated under reduced pressure to afford 1-[(2S)-3-(Acetylthio)-2-methyl-1-oxopropyl]-L-prolyl-L-phenylalanine tert-butyl ester (1.19 g, 66%) as pale yellow oil.

$^1$H-NMR (CDCl$_3$): 7.15 (m, 5H), 4.63 (m, 2H), 3.46 (m, 2H) 2.99 (m, 4H), 2.73 (m, 1H), 2.28 (s, 3H), 1.88 (m, 3H), 1.37 (s, 9H), 1.08 (d, 3H)

1-[(2S)-3-(Acetylthio)-2-methyl-1-oxopropyl]-L-prolyl-L-phenylalanine tert-butyl ester (1.19 g, 0.025 Mol) was dissolved in a solution of trifluoroacetic acid:CH$_2$Cl$_2$ (1:2, 30 ml) and the reaction was stirred at room temperature for 1 hour. Then it was evaporated under reduced pressure affording 1-[(2S)-3-(acetylthio)-2-methyl-1-oxopropyl]-L-prolyl-L-phenylalanine as a clear oil (1.00 g, 100%) that was used in the subsequent reaction without any further purification.

$^1$H-NMR (CDCl$_3$): 7.23 (m, 5H), 7.05 (d, 1H), 4.91 (m, 1H), 4.55 (m, 1H), 3.62 (m, 2H), 3.15 (m, 3H), 2.92 (m, 2H), 2.38 (s, 3H), 2.07 (m, 4H), 1.88 (m, 3H), 1.17 (d, 3H).

1-[(2S)-3-(acetylthio)-2-methyl-1-oxopropyl]-L-prolyl-L-phenylalanine (1.00 g, 0.025 Mol), 1-hydroxy-3-bromomethylbenzene (0.463 g, 0.025 Mol) and 4-dimethylaminopyridine (0.060 g, 0.005 Mol) were dissolved in CHCl$_3$ (10 ml) and the solution was cooled to 0° C. Dicyclohexylcarbodiimide (0.70 g, 0.033 Mol) was then added and the solution was slowly warmed to room temperature and stirred for 5 h. The crude material was concentrated and purified by flash chromatography eluting with EtOAc/n-Hexane 1:1, affording 1-[(2S)-3-(Acetylthio)-2-methyl-1-oxopropyl]-L-prolyl- L-phenylalanine 3-bromomethyl phenyl ester (i.e. Alacepril 3-bromomethyl phenyl ester) (1.00 g) as a white powder.

$^1$H-NMR (CDCl$_3$): 7.30 (m, 7H), 6.98 (m, 2H), 4.98 (m, 1H), 4.66 (m, 1H), 4.45 (s, 2H), 3.45 (m, 3H), 3.28 (m, 2H), 3.09 (m, 1H), 3.07 (m, 1H), 2.78 (m, 1H), 2.34 (s, 3H), 2.00 (m, 4H), 1.01 (d, 3H).

1-[(2S)-3-(Acetylthio)-2-methyl-1-oxopropyl]-L-prolyl-L-phenylalanine 3-bromomethyl phenyl ester (1.00 g, 0.017 Mol) was dissolved in CH$_3$CN (10 ml) and AgNO$_3$ (0.73 g, 0.043 Mol) was added in the dark, under nitrogen. The mixture was heated at 40–50° C. for 6 h. The salts were filtered off, the solution was diluted with CH$_2$Cl$_2$ and the organic phase was washed with H$_2$O (2×50 ml) and brine (50 ml), dried over Na$_2$SO$_4$ and concentrated. The crude material was purified by flash chromatography eluting with EtOAc/n-Hexane (1:1), affording the title compound as a dense oil (380 mg, 40%).

$^1$H-NMR (CDCl$_3$): 7.30 (m, 7H), 6.98 (m, 2H), 5.55 (s, 2H), 4.98 (m, 1H), 4.66 (m, 1H), 3.45 (m, 3H), 3.28 (m, 2H), 3.09 (m, 1H), 3.07 (m, 1H), 2.78 (m, 1H), 2.34 (s, 3H), 2.00 (m, 4H), 1.01 (d, 3H).

EXAMPLES 9a, 9b, 9c

Ex.9a). With the same procedure described in Example 9 but starting from 3-bromo propanol 1-[(2S)-3-(Acetylthio)-2-methyl-1-oxopropyl]-L-prolyl-L-phenylalanine 3-nitrooxypropyl ester (corresponding to compound 76) was obtained;

Ex. 9b). With the same procedure described in Example 9 but starting from 4-bromobutanol 1-[(2S)-3-(Acetylthio)-2-methyl-1-oxopropyl]-L-prolyl-L-phenylalanine 4-nitrooxybutyl ester (corresponding to compound 77) was obtained as a white solid;

Ex. 9c). With the same procedure described in Example 9 but starting from 4-bromomethylbenzyl alcohol 1-[(2S)-3-(Acetylthio)-2-methyl-1-oxopropyl]-L-prolyl-L-phenylalanine 4-nitrooxymethylbenzyl ester (corresponding to compound 79) was obtained as a white solid.

Pharmacological Experiments

EXAMPLE 10

Evaluation of the Vasorelaxing Activity of the Compounds According to the Invention and the Native ACE Inhibitor Captopril.

The tested compounds are the following:
1-[3-(Acetylthio)-(2S)-methyl-1-oxopropyl]-L-proline 3-nitrooxy propyl ester, (compound of Ex. 8)
1-[3-(acetylthio)-(2S)-methyl-1-oxopropyl]-L-proline 3-nitrooxymethylphenyl ester, (compound of Ex. 8b)
1-[(2S)-3-(Nitrooxymethoxycarbonyl) mercapto-2-methyl-1-oxopropyl]-L-proline, (compound of Ex. 3)
1-[(2S)-3-(4-Nitrooxybutoxycarbonyl) mercapto-2-methyl-1-oxopropyl]-L-proline, (compound of Ex. 2)
[(2S)-3-(Acetylthio)-2-methyl-1-oxopropyl]-L-prolyl-L-phenylalanine 3-nitrooxymethyl phenyl ester, (compound Ex. of 9)
captopril.

The ability of the captopril nitroderivatives of the invention to induce vasorelaxation was tested in vitro in isolated rabbit thoracic aorta preparations (Wanstall J. C. et al., Br. J. Pharmacol., 134:463–472, 2001). Male New Zealand rabbits were anaesthetized with thiopental-Na (50 mg/kg, iv), sacrificed by exsanguinations and then the thorax was opened and the aorta dissected. Single ring preparations (4 mm in length) of thoracic aorta were set up in physiological salt solution (PSS) at 37° C. in small organ chambers (5 ml). The composition of PSS was (mM): NaCl 130, NaHCO$_3$ 14.9, KH$_2$PO$_4$ 1.2, MgSO$_4$ 1.2, HEPES 10, CaCl$_2$, ascorbic acid 170 and glucose 1.1 (95% O$_2$/5% CO$_2$; pH 7.4). Each ring was mounted under 2 g passive tension. Isometric tension was recorded with a Grass transducer (Grass FT03) attached to a BIOPAC MP150 System. Preparations were allowed to equilibrate for 1 h, then contracted submaximally with noradrenaline (NA, 1 μM) and, when the contraction was stable, acetylcholine (ACh, 10 μM) was added. A relaxant response to ACh indicated the presence of a functional endothelium. Vessel that were unable to contract to NA or showed no relaxation to Ach were discarded. When a stable precontraction was reached, a cumulative concentration-response curve for each of the tested compounds was obtained in the presence of a functional endothelium. Time intervals between different concentrations were based on the time needed to reach a full response. Each arterial ring was exposed to only one combination of inhibitor and the tested compounds. Moreover, the effect of the soluble guanylyl cyclase inhibitor ODQ (1-H-(1,2,4)-oxadiazol (4,3-a)quinoxalin-1-one) on the dilator responses elicited by the compounds was examined preincubating the aortic rings with ODQ (10 μM) for 20 min.

Results are expressed as IC$_{50}$ value, which is the concentration of the tested compound producing 50% of the maximum relaxation, and as Emax value which is the maximum efficacy at a concentration of 100 μM of the tested compound.

During the experimental period, the plateau obtained with NA was stable without significant spontaneous loss of contraction in the aortic rings. Under these experimental conditions, the native ACE inhibitor, captopril, did not produce relaxation at any of the concentration tested, the curve being not different from that built up in presence of vehicle alone.

Furthermore, in experiments performed in presence of ODQ (10 μM), the vasorelaxant responses to all the tested compounds were inhibited.

TABLE 1

Vasorelaxing activity of the compounds according to the invention and of captopril

| Compound | Emax | IC$_{50}$ (μM) |
|---|---|---|
| Captopril | 0 | 0 |
| Compound of Ex. 8b | 92.4 ± 4.15 | 4.01 ± 1.18 |
| Compound of Ex. 8 | 77.9 ± 3.21 | 26.1 ± 3.91 |
| Compound of Ex. 3 | 97.9 ± 1.51 | 6.7 ± 0.84 |
| Compound of Ex. 2 | 96.9 ± 1.87 | 6.0 ± 0.87 |
| Compound of Ex. 9 | 96.8 ± 0.65 | 3.2 ± 0.65 |

EXAMPLE 11

Evaluation of Antihypertensive Activity and of the ACE Activity of the Compounds According to the Invention Versus Captopril in a Genetic Model of Hypertension (SHR Rats).

The tested compounds are the following:
1-[3-(Acetylthio)-(2S)-methyl-1-oxopropyl]-L-proline 3-nitrooxy propyl ester, (compound Ex. 8)
[3-(acetylthio)-(2S)-methyl-1-oxopropyl]-L-proline 3-nitrooxymethylphenyl ester, (compound in Ex. 8b)
captopril SHR rats were treated orally in a single dose of 30 mg/Kg. After 2 hours the animal were anaesthetized with tiopental-Na; a fluid catheter was inserted in a right carotid artery and connected to a transducer for the homodynamic measurements. 4 hours after the treatment the arterial pressure (MAP, mmHg) was measured. Results are reported in table 2.

As shown in Table 2, the nitroderivatives of the invention 1-[3-(Acetylthio)-(2S)-methyl-1-oxopropyl]-L-proline 3-nitrooxy propyl ester (compound Ex. 8) and 1-[3-(acetylthio)-(2S)-methyl-1-oxopropyl]-L-proline 3-nitrooxy methylphenyl ester (compound Ex. 8b), were able to reduce blood pressure by 35% and by 43% respectively vs the control at 4 hrs after treatment.

At the end of the experiments the blood was collected from the right carotid. The heparinized blood samples were centrifuged at 1000 g for 20 min at 4° C. The plasma was stored at −20° C. until the ACE activity measurements.

The ACE activity was determined by a spectrophotometric method (Sigma) based on the enzymatic reaction catalysed by ACE, where the FAPGG was hydrolysed to FAP.

FAPGG hydrolysis produced a decrease in the absorbance at 340 nm, a marker of ACE activity in the sample. Results, reported in table 3, were expressed as U/L in heparinized plasma.

As shown in Table 3, the compounds of the invention inhibited ACE activity in a better extent than captopril.

TABLE 2

Arterial pressure (MAP, mmHg) monitored at the 4$^{th}$ hours after the treatment.

| vehicle | Captopril | Comp. of Ex. 8 | Comp. of Ex. 8b |
|---|---|---|---|
| 202 | 145 | 132 | 116 |

TABLE 3

| | ACE activity (U/L) | | |
|---|---|---|---|
| vehicle | Captopril | Comp. of Ex. 8 | Comp. of Ex. 8b |
| 85 | 66 | 59 | 53 |

The invention claimed is:

1. A compound of general formula (I) and/or a pharmaceutically acceptable salt or stereoisomer thereof

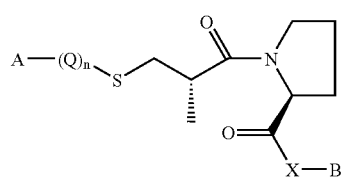

(I)

wherein:
Q=—CO—, —OCO—, —CONH—, —COCH(R)NH— wherein R is H, straight or branched ($C_1$–$C_6$)-alkyl, —$(CH_2)_2SCH_3$ or benzyl; with the proviso that —S— is bound to —CO—;
n is an integer equal to 0 or 1;
A=H, W (wherein W is $C_1$–$C_6$-alkyl, phenyl or benzyl) or is chosen from the following groups:

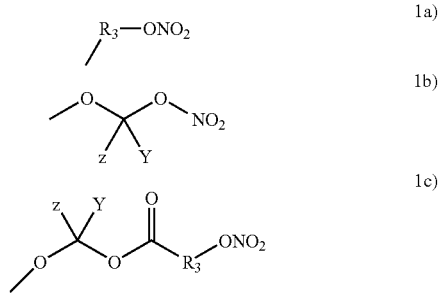

wherein z and Y are the same or different, and are H or straight or branched ($C_1$–$C_4$)-alkyl; with the proviso that when A is selected from the groups 1b and 1c, Q=—CO—;

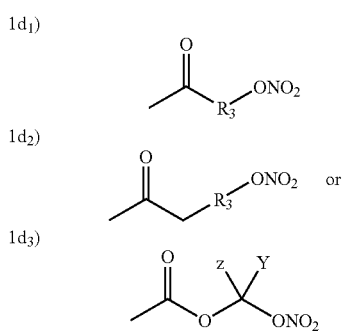

wherein z and Y are as above defined;
with the proviso that when A is selected from the groups $1d_1$–$1d_3$, Q=—COCH(R)NH—
wherein R is as above defined;
$R_3$ is a bivalent radical having the following meanings:
a) straight or whenever possible branched $C_1$–$C_{20}$ alkylene, optionally substituted with at least an halogen atom or an optionally substituted cycloalkylene having from 5 to 7 carbon atoms;

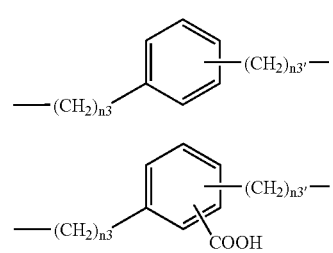

wherein:
n3 is an integer from 0 to 20;
n3' is an integer from 1 to 20;
wherein the —$ONO_2$ group is bound to a —$CH_2$ group;

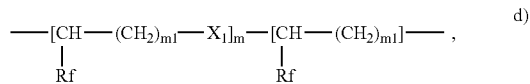

-continued

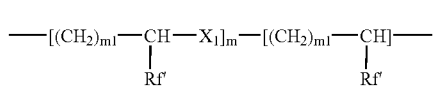
d₁)

wherein X₁ is —O— or —S—, m is an integer from 1 to 6, m₁ is an integer from 1 to 10, Rf is a hydrogen atom or CH₃, Rf' is CH₃; or

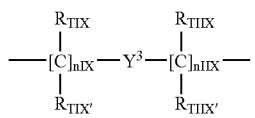
e)

wherein:
nIX is an integer from 0 to 10;
nIIX is an integer from 1 to 10;
$R_{TIX}$, $R_{TIX'}$, $R_{TIIX}$, $R_{TIIX'}$, are the same or different, and are H or straight or branched ($C_1$–$C_4$-alkyl;
and wherein the —ONO₂ group is bound to

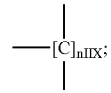

$Y^3$ is a heterocyclic saturated, unsaturated or aromatic 5 or 6 members ring, containing one or more heteroatoms selected from nitrogen, oxygen, and sulphur,
X=—O—, —S—;
B=H, —$R_{3a}$—ONO₂ wherein $R_{3a}$ has the same meaning of $R_3$ as above defined or is chosen from the following groups:

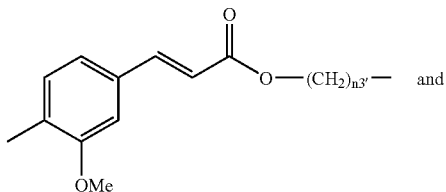
f)

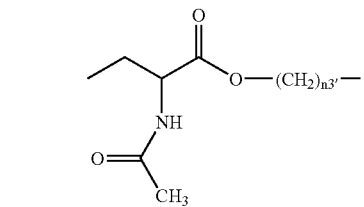
g)

wherein n3' is as above defined; wherein the —ONO₂ group is bound to the group —(CH₂)$_{n3'}$;
wherein $R_2$ is H, a straight or branched ($C_1$–$C_6$)-alkyl or —$R_{3b}$—ONO₂, $R_{3b}$ has the same meaning of $R_3$ as above defined in a);
provided that:
i) when $R_{3a}$ is the group as defined in f) and g) then A is W;
ii) when $R_{3a}$ is the group as defined in g) then X is —S—;
iii) at least one of the groups A or B contains a —ONO₂ group.

2. A compound of general formula (I) and/or a pharmaceutically acceptable salt or stereoisomer thereof according to claim 1 wherein:
Q=—CO—, —OCO—, —CONH— or, —COCH(R)NH— wherein R is H or CH₃; with the proviso that —S— is bound to —CO;
n is an integer equal to 0 or 1;
A=H, W (wherein W is $C_1$–$C_6$-alkyl) or is chosen from the following groups:

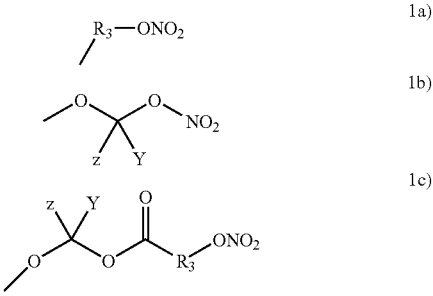
1a)
1b)
1c)

wherein z and Y are the same or different, and are H or CH₃; with the proviso that when A is selected from the groups 1b and 1c, Q=—CO—;

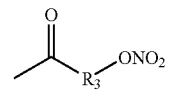
1d₁)

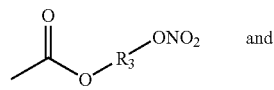
1d₂)
and

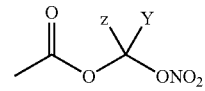
1d₃)

wherein z and Y are as above defined;
with the proviso that when A is selected from groups 1d₁–1d₃, Q=—COCH(R)NH— where R is as above defined;
$R_3$ is a bivalent radical having the following meanings:
a) straight $C_1$–$C_6$ alkylene;

b)
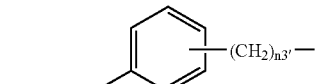

c)
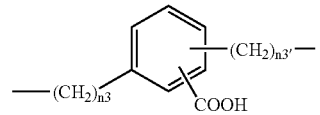

wherein:

n3 is an integer from 0 to 5 and n3' is an integer from 1 to 5;

wherein the —ONO$_2$ group is bound to a —CH$_2$ group;

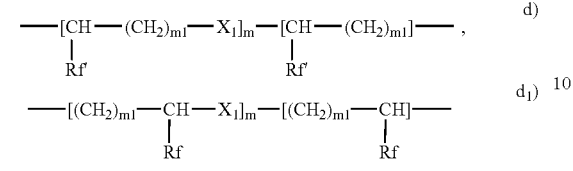
d)

d$_1$)

wherein X$_1$ is —O— or —S—, m is an integer from 1 to 6, m$_1$ is an integer from 1 to 10, Rf is a hydrogen atom or CH$_3$, Rf' is CH$_3$;

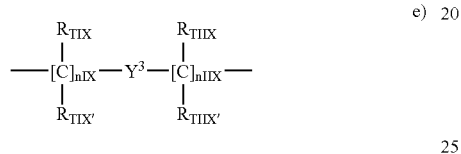
e)

wherein:

nIX is an integer from 0 to 3 and nIIX is an integer from 1 to 3;

R$_{TIX}$, R$_{TIX'}$, R$_{TIIX}$, R$_{TIIX'}$ are the same and are H;

wherein the —ONO$_2$ group is bound to a —CH$_2$ group;

Y$^3$ is an heterocyclic saturated, unsaturated or aromatic, containing one or more atoms of nitrogen and selected from Y1–Y6 as defined in claim 1, X=—O—, —S—; and B=H, —R$_{3a}$—ONO$_2$ wherein R$_{3a}$ has the same meaning of R$_3$ as above defined or is chosen from the following groups:

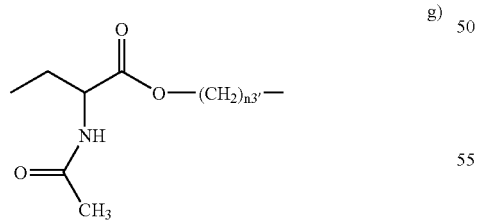
f)

g)

wherein n3' is as above defined wherein the —ONO$_2$ group is bound to the group —(CH$_2$)$_{n3'}$;

wherein R$_2$ is H, a straight or branched (C$_1$–C$_6$)-alkyl or —R$_{3b}$—ONO$_2$, and R$_{3b}$ has the same meaning of R$_3$ as above defined in a).

3. A compound of general formula (I) and/or a pharmaceutically acceptable or stereoisomer thereof according to claim 1 wherein:

Q=—CO—, —OCO—, —CONH—, or —COCH(R)NH— wherein R is H or CH$_3$; with the proviso that —S— is bound to —CO;

n is 1;

A is chosen from the following groups:

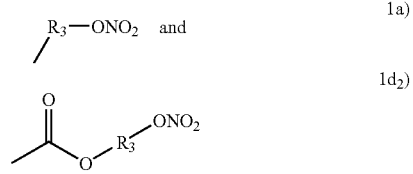
1a)

1d$_2$)

with the proviso that when A is selected from group 1d$_2$, Q=—COCH(R)NH— where R is as above defined;

R$_3$ is a bivalent radical having the following meanings:

a) straight or branched C$_1$–C$_6$ alkylene; or

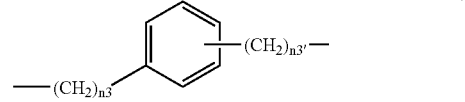
b)

wherein:

n3 is 0 or 1 and n3' is 1;

wherein the —ONO$_2$ group is bound to a —CH$_2$ group;

X=—O—; and

B=H.

4. A compound of general formula (I) and/or a pharmaceutically acceptable salt or stereoisomer thereof according to claim 1 wherein:

Q=—CO—;

n is 1;

A is CH$_3$;

X=—O—; and

B is —R$_{3a}$—ONO$_2$ wherein R$_{3a}$ have the following meanings:

a) straight C$_1$–C$_6$ alkylene;

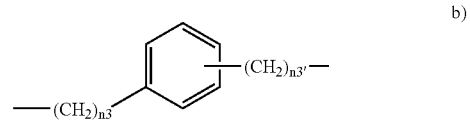
b)

wherein:

n3 is 0 or 1 and n3' is 1;

wherein the —ONO$_2$ group is bound to a —CH$_2$ group.

5. A compound according to claim 1, selected from the group consisting of:

(1) A compound of formula (I) wherein Q=—CO—, n=1, A is the group as defined in 1a) wherein R$_3$ is a straight C$_3$ alkylene, X=—O— and B is H;

(2) A compound of formula (I) wherein Q=—CO—, n=1, A is the group as defined in 1a) wherein R$_3$ is a straight C$_4$ alkylene, X=—O— and B is H;

(3) A compound of formula (I) wherein Q=—CO—, n=1, A is the group as defined in 1a) wherein R$_3$ is the group as defined in b) wherein n3 is an integer equal to 0 and n3' is an integer equal to 1, X=—O— and B is H;

(4) A compound of formula (I) wherein Q=—OCO—, n=1, A is the group as defined in 1a) wherein $R_3$ is a straight $C_4$ alkylene, X=—O— and B is H;

(5) A compound of formula (I) wherein Q=—OCO—, n=1, A is the group as defined in 1a) wherein $R_3$ is a straight $C_3$ alkylene, X=—O— and B is H;

(6) A compound of formula (I) wherein Q=—OCO—, n=1, A is the group as defined in 1a) wherein $R_3$ is the group as defined in b) wherein n3 is an integer equal to 0 and n3' is an integer equal to 1, X=—O— and B is H;

(7) A compound of formula (I) wherein Q=—CO—, n=1, A is the group as defined in 1b) wherein z is H and Y is $CH_3$, X=—O— and B is H;

(8) A compound of formula (I) wherein Q=—CO—, n=1, A is the group as defined in 1b) wherein z and Y are H, X=—O— and B is H;

(9) A compound of formula (I) wherein Q=—CO—, n=1, A is the group as defined in 1c) wherein z and Y are H, $R_3$ is the group as defined in b) wherein n3 is an integer equal to 0 and n3' is an integer equal to 1, X=—O— and B is H;

(10) A compound of formula (I) wherein Q=—COCH(R)NH— with R=$CH_3$, n=1, A is the group as defined in $1d_1$) wherein $R_3$ is a straight $C_4$ alkylene, X=—O— and B is H;

(11) A compound of formula (I) wherein Q=—COCH(R)NH— with R=$CH_3$, n=1, A is the group as defined in $1d_1$) wherein $R_3$ is a straight $C_3$ alkylene, X=—O— and B is H;

(12) A compound of formula (I) wherein Q=—COCH(R)NH— with R=H, n=1, A is the group as defined in $1d_1$) wherein $R_3$ is a straight $C_3$ alkylene, X=—O— and B is H;

(13) A compound of formula (I) wherein Q=—COCH(R)NH— with R=H, n=1, A is the group as defined in $1d_1$) wherein $R_3$ is a straight $C_4$ alkylene, X=—O— and B is H;

(14) A compound of formula (I) wherein Q=—COCH(R)NH— with R=$CH_3$, n=1, A is the group as defined in $1d_1$) wherein $R_3$ is the group as defined in b) wherein n3 is an integer equal to 0 and n3' is an integer equal to 1, X=—O— and B is H; —(15) A compound of formula (I) wherein Q=—COCH(R)NH— with R=H, n=1, A is the group as defined in $1d_1$) wherein $R_3$ is the group as defined in b) wherein n3 is an integer equal to 0 and n3' is an integer equal to 1, X=—O— and B is H;

(16) A compound of formula (I) wherein Q=—COCH(R)NH— with R=$CH_3$, n=1, A is the group as defined in $1d_2$) wherein $R_3$ is a straight $C_4$ alkylene, X=—O— and B is H;

(17) A compound of formula (I) wherein Q=—COCH(R)NH— with R=$CH_3$, n=1, A is the group as defined in $1d_2$) wherein $R_3$ is a straight $C_3$ alkylene, X=—O— and B is H;

(18) A compound of formula (I) wherein Q=—COCH(R)NH— with R=$CH_3$, n=1, A is the group as defined in $1d_3$) wherein z is H and Y is $CH_3$, X=—O— and B is H;

(19) A compound of formula (I) wherein Q=—COCH(R)NH— with R=$CH_3$, n=1, A is the group as defined in $1d_3$) wherein z and Y are H, X=—O— and B is H;

(20) A compound of formula (I) wherein Q=—COCH(R)NH— with R=H, n=1, A is the group as defined in $1d_2$) wherein $R_3$ is a straight $C_4$ alkylene, X=—O— and B is H;

(21) A compound of formula (I) wherein Q=—COCH(R)NH— with R=H, n=1, A is the group as defined in $1d_2$) wherein $R_3$ is a straight $C_3$ alkylene, X=—O— and B is H;

(22) A compound of formula (I) wherein Q=—COCH(R)NH— with R=H, n=1, A is the group as defined in $1d_3$) wherein z is H and Y is $CH_3$, X=—O— and B is H;

(23) A compound of formula (I) wherein Q=—COCH(R)NH— with R=H, n=1, A is the group as defined in $1d_3$) wherein z and Y are H, X=—O— and B is H;

(24) A compound of formula (I) wherein Q=—COCH(R)NH— with R=$CH_3$, n=1, A is the group as defined in $1d_2$) wherein $R_3$ is the group as defined in b) wherein n3 is an integer equal to 0 and n3' is an integer equal to 1, X=—O— and B is H;

(25) A compound of formula (I) wherein Q=—COCH(R)NH— with R=H, n=1, A is the group as defined in $1d_2$) wherein $R_3$ is the group as defined in b) wherein n3 is an integer equal to 0 and n3' is an integer equal to 1, X=—O— and B is H;

(26) A compound of formula (I) wherein Q=—COCH(R)NH— with R=$CH_3$, n=1, A is the group as defined in $1d_1$) wherein $R_3$ is a straight $C_4$ alkylene, X=—O— and B=—$R_{3a}$—$ONO_2$ wherein $R_{3a}$ is a straight $C_3$ alkylene;

(27) A compound of formula (I) wherein Q=—COCH(R)NH— with R=$CH_3$, n=1, A is the group as defined in $1d_1$) wherein $R_3$ is a straight $C_3$ alkylene, X=—O— and B=—$R_{3a}$—$ONO_2$ wherein $R_{3a}$ is a straight $C_3$ alkylene;

(28) A compound of formula (I) wherein Q=—COCH(R)NH— with R=$CH_3$, n=1, A is the group as defined in $1d_1$) wherein $R_3$ is a straight $C_3$ alkylene, X=—O— and B=—$R_{3a}$—$ONO_2$ wherein $R_{3a}$ is the group as defined in b) wherein n3 is an integer equal to 0 and n3' is an integer equal to 1;

(29) A compound of formula (I) wherein Q=—COCH(R)NH— with R=$CH_3$, n=1, A is the group as defined in $1d_1$) wherein $R_3$ is a straight $C_4$ alkylene, X=—O— and B=—$R_{3a}$—$ONO_2$ wherein $R_{3a}$ is the group as defined in b) wherein n3 is an integer equal to 0 and n3' is an integer equal to 1;

(30) A compound of formula (I) wherein Q=—COCH(R)NH— with R=H, n=1, A is the group as defined in $1d_1$) wherein $R_3$ is a straight $C_4$ alkylene, X=—O— and B=—$R_{3a}$—$ONO_2$ wherein $R_{3a}$ is a straight $C_3$ alkylene;

(31) A compound of formula (I) wherein Q=—COCH(R)NH— with R=H, n=1, A is the group as defined in $1d_1$) wherein $R_3$ is a straight $C_3$ alkylene, X=—O— and B=—$R_{3a}$—$ONO_2$ wherein $R_{3a}$ is a straight $C_3$ alkylene;

(32) A compound of formula (I) wherein Q=—COCH(R)NH— with R=H, n=1, A is the group as defined in $1d_1$) wherein $R_3$ is a straight $C_3$ alkylene, X=—O— and B=—$R_{3a}$—$ONO_2$ wherein $R_{3a}$ is the group as defined in b) wherein n3 is an integer equal to 0 and n3' is an integer equal to 1;

(33) A compound of formula (I) wherein Q=—COCH(R)NH— with R=H, n=1, A is the group as defined in $1d_1$) wherein $R_3$ is a straight $C_4$ alkylene, X=—O— and B=—$R_{3a}$—$ONO_2$ wherein $R_{3a}$ is the group as defined in b) wherein n3 is an integer equal to 0 and n3' is an integer equal to 1;

(34) A compound of formula (I) wherein Q=—COCH(R)NH— with R=$CH_3$, n=1, A is the group as defined in $1d_1$) wherein $R_3$ is a straight $C_4$ alkylene, X=—O— and B=—$R_{3a}$—$ONO_2$ wherein $R_{3a}$ is a straight $C_4$ alkylene;

(35) A compound of formula (I) wherein Q=—COCH(R)NH— with R=H, n=1, A is the group as defined in $1d_1$)

wherein $R_3$ is a straight $C_4$ alkylene, X=—O— and B=—$R_{3a}$—$ONO_2$ wherein $R_{3a}$ is a straight $C_4$ alkylene;
(36) A compound of formula (I) wherein Q=—COCH(R)NH— with R=$CH_3$, n=1, A is the group as defined in $1d_1$) wherein $R_3$ is a straight $C_3$ alkylene, X=—O— and B=—$R_{3a}$—$ONO_2$ wherein $R_{3a}$ is a straight $C_4$ alkylene;
(37) A compound of formula (I) wherein Q=—COCH(R)NH— with R=H, n=1, A is the group as defined in $1d_1$) wherein $R_3$ is a straight $C_3$ alkylene, X=—O— and B=—$R_{3a}$—$ONO_2$ wherein $R_{3a}$ is a straight $C_4$ alkylene;
(38) A compound of formula (I) wherein Q=—COCH(R)NH— with R=$CH_3$, n=1, A is H, X=—O— and B=—$R_{3a}$—$ONO_2$ wherein $R_{3a}$ is a straight $C_4$ alkylene;
(39) A compound of formula (I) wherein Q=—COCH(R)NH— with R=$CH_3$, n=1, A is H, X=—O— and B=—$R_{3a}$—$ONO_2$ wherein $R_{3a}$ is a straight $C_3$ alkylene;
(40) A compound of formula (I) wherein Q=—COCH(R)NH— with R=$CH_3$, n=1, A is H, X=—O— and B=—$R_{3a}$—$ONO_2$ wherein $R_{3a}$ is the group as defined in b) wherein n3 is an integer equal to 0 and n3' is an integer equal to 1;
(41) A compound of formula (I) wherein Q=—COCH(R)NH— with R=$CH_3$, n=1, A is H, X=—O— and B=—$R_{3a}$—$ONO_2$ wherein $R_{3a}$ is the group as defined in b) wherein n3 and n3' are an integer equal to 1;
(42) A compound of formula (I) wherein Q=—COCH(R)NH— wherein R and A are H, n=1, X=—O— and B=—$R_{3a}$—$ONO_2$ wherein $R_{3a}$ is a straight $C_3$ alkylene;
(43) A compound of formula (I) wherein Q=—COCH(R)NH— wherein R and A are H, n=1, X=—O— and B=—$R_{3a}$—$ONO_2$ wherein $R_{3a}$ is a straight $C_4$ alkylene;
(44) A compound of formula (I) wherein Q=—COCH(R)NH— wherein R and A are H, n=1, X=—O— and B=—$R_{3a}$—$ONO_2$ wherein $R_{3a}$ is the group as defined in b) wherein n3 is an integer equal to 0 and n3' is an integer equal to 1;
(45) A compound of formula (I) wherein Q=—COCH(R)NH— wherein R and A are H, n=1, X=—O— and B=—$R_{3a}$—$ONO_2$ wherein $R_{3a}$ is the group as defined in b) wherein n3 and n3' are an integer equal to 1;
(46) A compound of formula (I) wherein Q=—CO—, n=1, A is the group as defined in 1a) wherein $R_3$ is a straight $C_3$ alkylene, X=—O— and B is =—$R_{3a}$—$ONO_2$ wherein $R_{3a}$ is a straight $C_3$ alkylene;
(47) A compound of formula (I) wherein Q=—CO—, n=1, A is the group as defined in 1a) wherein $R_3$ is a straight $C_3$ alkylene, X=—O— and B is =—$R_{3a}$—$ONO_2$ wherein $R_{3a}$ is a straight $C_4$ alkylene;
(48) A compound of formula (I) wherein Q=—CO—, n=1, A is the group as defined in 1a) wherein $R_3$ is a straight $C_3$ alkylene, X=—O— and B is =—$R_{3a}$—$ONO_2$ wherein $R_{3a}$ is the group as defined in b) wherein n3 is an integer equal to 0 and n3' is an integer equal to 1;
(49) A compound of formula (I) wherein Q=—CO—, n=1, A is the group as defined in 1a) wherein $R_3$ is a straight $C_4$ alkylene, X=—O— and B is =—$R_{3a}$—$ONO_2$ wherein $R_{3a}$ is the group as defined in b) wherein n3 is an integer equal to 0 and n3' is an integer equal to 1;
(50) A compound of formula (I) wherein Q=—CO—, n=1, A is the group as defined in 1a) wherein $R_3$ is a straight $C_4$ alkylene, X=—O— and B is =—$R_{3a}$—$ONO_2$ wherein $R_{3a}$ is a straight $C_4$ alkylene;
(51) A compound of formula (I) wherein Q=—CO—, n=1, A is the group as defined in 1a) wherein $R_3$ is a straight $C_4$ alkylene, X=—O— and B is =—$R_{3a}$—$ONO_2$ wherein $R_{3a}$ is a straight $C_3$ alkylene;
(52) A compound of formula (I) wherein Q=—OCO—, n=1, A is the group as defined in 1a) wherein $R_3$ is a straight $C_3$ alkylene, X=—O— and B is =—$R_{3a}$—$ONO_2$ wherein $R_{3a}$ is a straight $C_3$ alkylene;
(53) A compound of formula (I) wherein Q=—OCO—, n=1, A is the group as defined in 1a) wherein $R_3$ is a straight $C_4$ alkylene, X=—O— and B is =—$R_{3a}$—$ONO_2$ wherein $R_{3a}$ is a straight $C_4$ alkylene;
(54) A compound of formula (I) wherein Q=—OCO—, n=1, A is the group as defined in 1a) wherein $R_3$ is a straight $C_3$ alkylene, X=—O— and B is =—$R_{3a}$—$ONO_2$ wherein $R_{3a}$ is the group as defined in b) wherein n3 is an integer equal to 0 and n3' is an integer equal to 1;
(55) A compound of formula (I) wherein Q=—OCO—, n=1, A is the group as defined in 1a) wherein $R_3$ is a straight $C_4$ alkylene, X=—O— and B is =—$R_{3a}$—$ONO_2$ wherein $R_{3a}$ is the group as defined in b) wherein n3 is an integer equal to 0 and n3' is an integer equal to 1;
(56) A compound of formula (I) wherein Q=—OCO—, n=1, A is the group as defined in 1a) wherein $R_3$ is a straight $C_3$ alkylene, X=—O— and B is =—$R_{3a}$—$ONO_2$ wherein $R_{3a}$ is a straight $C_4$ alkylene;
(57) A compound of formula (I) wherein Q=—OCO—, n=1, A is the group as defined in 1a) wherein $R_3$ is a straight $C_4$ alkylene, X=—O— and B is =—$R_{3a}$—$ONO_2$ wherein $R_{3a}$ is a straight $C_3$ alkylene;
(58) A compound of formula (I) wherein Q=—CO—, n=1, A=W wherein W is $CH_3$, X=—O— and B is =$R_{3a}$—$ONO_2$ wherein $R_{3a}$ is a straight $C_4$ alkylene;
(59) A compound of formula (I) wherein Q=—OCO—, n=1, A =W wherein W is $CH_3$, X=—O— and B is =—$R_{3a}$—$ONO_2$ wherein $R_{3a}$ is a straight $C_3$ alkylene;
(60) A compound of formula (I) wherein Q=—CO—, n=1, A =W wherein W is $CH_3$, X=—O— and B is =—$R_{3a}$—$ONO_2$ wherein $R_{3a}$ is the group as defined in b) wherein n3 is an integer equal to 0 and n3' is an integer equal to 1;
(61) A compound of formula (I) wherein Q=—CO—, n=1, A =W wherein W is $CH_3$, X=—O— and B is =—$R_{3a}$—$ONO_2$ wherein $R_{3a}$ is the group as defined in b) wherein n3 and n3' are an integer equal to 1;
(62) A compound of formula (I) wherein Q=—CO—, n=1, A is the group as defined in 1b) wherein z and Y are H, X=—O— and B is =—$R_{3a}$—$ONO_2$ wherein $R_{3a}$ is a straight $C_3$ alkylene;
(63) A compound of formula (I) wherein Q=—CO—, n=1, A is the group as defined in 1b) wherein z is H and Y is $CH_3$, X=—O— and B is =—$R_{3a}$—$ONO_2$ wherein $R_{3a}$ is a straight $C_3$ alkylene;
(64) A compound of formula (I) wherein Q=—CO—, n=1, A is the group as defined in 1b) wherein z and Y are H, X=—O— and B is =—$R_{3a}$—$ONO_2$ wherein $R_{3a}$ is a straight $C_4$ alkylene;
(65) A compound of formula (I) wherein Q=—CO—, n=1, A is the group as defined in 1b) wherein z is H and Y is $CH_3$, X=—O— and B is =—$R_{3a}$—$ONO_2$ wherein $R_{3a}$ is a straight $C_4$ alkylene;
(66) A compound of formula (I) wherein Q=—CO—, n=1, A=W wherein W is $CH_3$, X=—S— and B is =—$R_{3a}$—$ONO_2$ wherein $R_{3a}$ is the group as defined in g) wherein n3' is an integer equal to 4;
(67) A compound of formula (I) wherein Q=—CO—, n=1, A=W wherein W is $CH_3$, X=—O— and B is =—$R_{3a}$—$ONO_2$ wherein $R_{3a}$ is the group as defined in f) wherein n3' is an integer equal to 4; and

(81) A compound of formula (I) wherein Q=—CO—, n=1, A=W wherein W is $CH_3$, X=—O— and B is =—$R_{3a}ONO_2$ wherein $R_{3a}$ is a straight $C_5$ alkylene.

6. A process for preparing a compound of general formula (I) as defined in claim 1, or a pharmaceutically acceptable salt or stereoisomer thereof, which process comprises:

i) reacting a compound of formula (II):

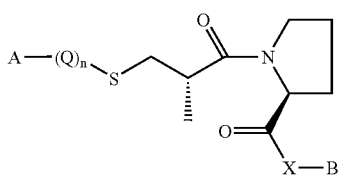

wherein:

Q and n are as defined in claim 1;

A=H, W wherein W is as defined in claim 1, an aminic protecting group or is chosen from the following groups:

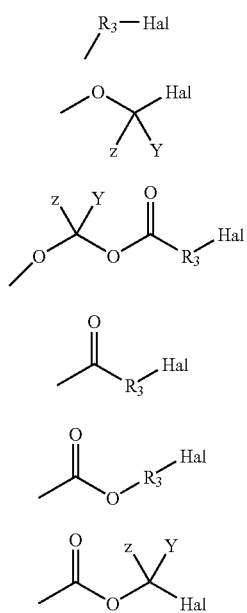

wherein $R_3$, z and Y are as defined in claim 1;

X is as defined in claim 1;

B=H, carboxylic protecting group, —$R_{3a}$-Hal wherein $R_{3a}$ is as defined in claim 1 or B is the group of formula (IA) as defined in claim 1, wherein $R_2$ is H, a straight or branched $(C_1-C_6)$-alkyl or —$R_{3b}$-Hal wherein $R_{3b}$ is as defined in claim 1; and Hal is an halogen, with $AgNO_3$ in a suitable organic solvent such as acetonitrile or tetrahydrofuran (THF) under nitrogen at temperatures range between 20°–80° C. and ii) optionally acid hydrolysing the carboxylic or aminic protecting group and iii) if desired, converting the resulting compound of general formula (I) into a pharmaceutically acceptable salt thereof.

7. A method for the treatment of acute coronary syndromes, stroke, pulmonary hypertension, hypertension, ocular hypertension, diabetic nephropathy, or peripheral vascular diseases medicated by the inhibition of angotensin converting enzyme comprising administering an effective amount a compound of general formula (I) and/or a salt or stereoisomer thereof according to claim 1 to a patient in need thereof.

8. A pharmaceutical composition comprising a pharmaceutically acceptable carrier and a pharmaceutically effective amount of a compound of general formula (I) and/or a salt or stereoisomer thereof according to claim 1.

9. A composition according to claim 8 in a suitable form for the oral, parenteral, rectal, topic and transdermic administration, by inhalation spray or aerosol or iontophoresis devices.

10. Liquid or solid pharmaceutical composition for oral, parenteral, rectal, topic and transdermic administration or inhalation in the form of tablets, capsules and pills eventually con enteric coating, powders, granules, gels, emulsions, solutions, suspensions, syrups, elixir, injectable forms, suppositories, in transdermal patches or liposomes, containing a compound of formula (I) according to claim 1 and/or a salt or stereoisomer thereof and a pharmaceutically acceptable carrier.

11. Pharmaceutical composition comprising a compound of formula I as defined in claim 1, a compound used to treat cardiovascular disease and a pharmaceutical acceptable excipient.

12. Pharmaceutical composition according to claim 11 wherein the compound used to treat cardiovascular disease is selected from the group consisting of beta adrenergic blockers, calcium channel blockers, angiotensin II receptor antagonists, antithrombotics, HMGCoA reductase inhibitors, aspirin or nitrooxyderivatives of aspirin, nitrosated beta blockers, nitrosated or nitrosilated calcium channel blockers.

13. A pharmaceutical kit for simultaneous, successively or previously administration of a composition according to claim 8 and a compound used to treat cardiovascular disease.

14. A compound of general formula (I) and/or a pharmaceutically acceptable salt or stereoisomer thereof according to claim 1 wherein $R_3$ is straight or whenever possible branched $C_1-C_5$ alkylene, optionally substituted with at least an halogen atom.

15. A compound of general formula (I) and/or a pharmaceutically acceptable salt or stereoisomer thereof according to claim 1 wherein n3 is an integer from 0 to 5.

16. A compound of general formula (I) and/or a pharmaceutically acceptable salt or stereoisomer thereof according to claim 1 wherein n3' is an integer from 1 to 5.

17. A compound of general formula (I) and/or a pharmaceutically acceptable salt or stereoisomer thereof according to claim 1 wherein m is an integer from 1 to 4.

18. A compound of general formula (I) and/or a pharmaceutically acceptable salt or stereoisomer thereof according to claim 1 wherein $m_1$ is an integer from 1 to 5.

19. A compound of general formula (I) and/or a pharmaceutically acceptable salt or stereoisomer thereof according to claim 1 wherein nIX is an integer from 0 to 3.

20. A compound of general formula (I) and/or a pharmaceutically acceptable salt or stereoisomer thereof according to claim 1 wherein nIIX is an integer from 1 to 3.

21. A compound of general formula (I) and/or a pharmaceutically acceptable salt or stereoisomer thereof according to claim 1 $R_{TIX}$, $R_{TIX'}$, $R_{TIIX}$, $R_{TIIX'}$ are H.

22. A compound of general formula (I) and/or a pharmaceutically acceptable salt or stereoisomer thereof according to claim 1 wherein $Y^3$ is

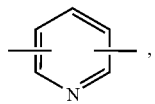 (Y1)

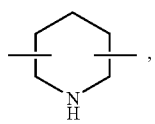 (Y2)

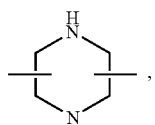 (Y3)

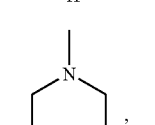 (Y4)

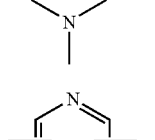 (Y5)

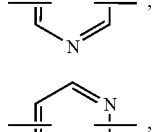 (Y6)

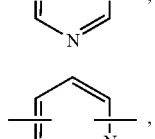 (Y7)

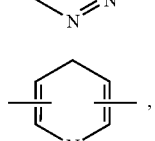 (Y8)

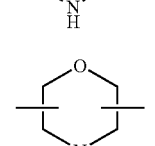 (Y9)

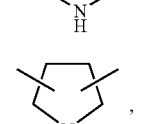 (Y10)

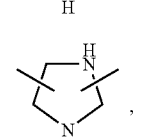 (Y11)

-continued

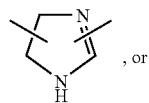 (Y12)

, or

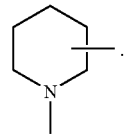 (Y13)

23. A compound of general formula (I) and/or a pharmaceutically acceptable salt or stereoisomer thereof

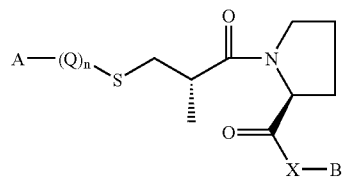 (I)

wherein:
Q=—CO—, —OCO—, —CONH—, —COCH(R)NH— wherein R is H, straight or branched ($C_1$–$C_6$)-alkyl, —(CH$_2$)$_2$SCH$_3$ or benzyl; with the proviso that —S— is bound to —CO;
n is an integer equal to 0 or 1;
A is chosen from the following groups:

1a) 

1b) 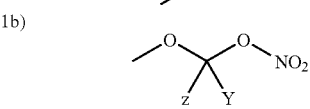

1c) 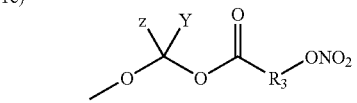

wherein z and Y are the same or different, and are H or straight or branched ($C_1$–$C_4$)-alkyl; with the proviso that when A is selected from the groups 1b and 1c, Q=—CO—;

1d$_1$) 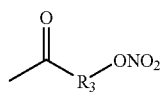

1d$_2$) 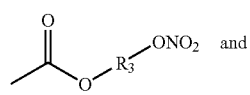 and

1d$_3$) 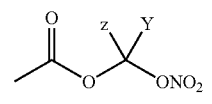

wherein z and Y are as above defined;
with the proviso that when A is selected from the groups $1d_1$–$1d_3$, Q=—COCH(R)NH— wherein R is as above defined;
$R_3$ is a bivalent radical having the following meanings:
a) straight or whenever possible branched $C_1$–$C_{20}$ alkylene, optionally substituted with at least an halogen atom, or an optionally substituted cycloalkylene having from 5 to 7 carbon atoms;

b)
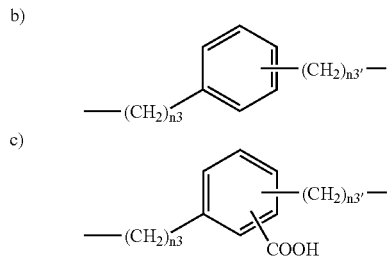

c)
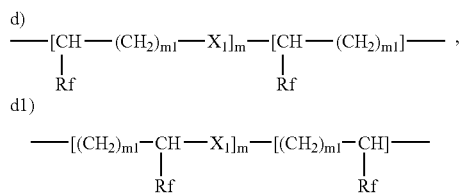

wherein:
n3 is an integer from 0 to 20;
n3' is an integer from 1 to 20;
wherein the —$ONO_2$ group is bound to a —$CH_2$ group;

d)
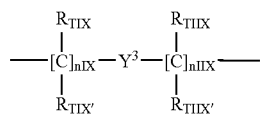

d1)

—[(CH$_2$)$_{m1}$—CH—X$_1$]$_m$—[(CH$_2$)$_{m1}$—CH]—
           |                       |
           Rf                    Rf wherein $X_1$ is —O— or —S—, m is an integer from 1 to 6, $m_1$ is an integer from 1 to 10, Rf is a hydrogen atom or $CH_3$, Rf' is $CH_3$; or e)

—[C]$_{nIX}$—Y$^3$—[C]$_{nIIX}$— with $R_{TIX}$, $R_{TIX'}$ above and $R_{TIIX}$, $R_{TIIX'}$ below wherein:
nIX is an integer from 0 to 10;
nIIX is an integer from 1 to 10;
$R_{TIX}$, $R_{TIX'}$, $R_{TIIX}$, $R_{TIIX'}$, are the same or different, and are H or straight or branched ($C_1$–$C_4$)-alkyl;
and wherein the —$ONO_2$ group is bound to —[C]$_{nIIX}$;

$Y^3$ is a heterocyclic saturated, unsaturated or aromatic 5 or 6 members ring, containing one or more heteroatoms selected from nitrogen, oxygen, sulphur,
X=—NH—, —O—, —S—; and
B=H, —$R_{3a}$—$ONO_2$ wherein $R_{3a}$ has the same meaning of $R_3$ as above defined; or B is the group of formula (IA):

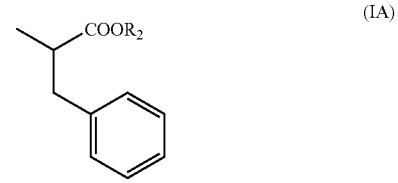

(IA)

wherein $R_2$ is H, a straight or branched ($C_1$–$C_6$)-alkyl or —$R_{3b}$—$ONO_2$, $R_{3b}$ has the same meaning of $R_3$ as above defined in a);
provided that when B is the group of formula (IA) then X is —NH—.

24. A compound according to claim 23, selected from the group consisting of:

(68) A compound of formula (I) wherein Q=—CO—, n=1, A is the group as defined in 1a) wherein $R_3$ is a straight $C_4$ alkylene, X=—NH— and B is the group of formula (IA) wherein $R_2$ is H;

(69) A compound of formula (I) wherein Q=—CO—, n=1, A is the group as defined in 1a) wherein $R_3$ is a straight $C_3$ alkylene, X=—NH— and B is the group of formula (IA) wherein $R_2$ is H;

(70) A compound of formula (I) wherein Q=—CO—, n=1, A is the group as defined in 1a) wherein $R_3$ is the group as defined in b) wherein n3 is an integer equal to 0 and n3' is an integer equal to 1, X=—NH— and B is the group of formula (IA) wherein $R_2$ is H;

(71) A compound of formula (I) wherein Q=—OCO—, n=1, A is the group as defined in 1a) wherein $R_3$ is a straight $C_4$ alkylene, X=—NH— and B is the group of formula (IA) wherein $R_2$ is H;

(72) A compound of formula (I) wherein Q=—OCO—, n=1, A is the group as defined in 1a) wherein $R_3$ is a straight $C_3$ alkylene, X=—NH— and B is the group of formula (IA) wherein $R_2$ is H;

(73) A compound of formula (I) wherein Q=—OCO—, n=1, A is the group as defined in 1a) wherein $R_3$ is the group as defined in b) wherein n3 is an integer equal to 0 and n3' is an integer equal to 1, X=—NH— and B is the group of formula (IA) wherein $R_2$ is H;

(74) A compound of formula (I) wherein Q=—CO—, n=1, A is the group as defined in 1b) wherein z and Y are H, X=—NH— and B is the group of formula (IA) wherein $R_2$ is H; and

(75) A compound of formula (I) wherein Q=—CO—, n=1, A is the group as defined in 1b) wherein z is H and Y is $CH_3$, X=—NH— and B is the group of formula (IA) wherein $R_2$ is H.

* * * * *

UNITED STATES PATENT AND TRADEMARK OFFICE
CERTIFICATE OF CORRECTION

PATENT NO. : 7,169,805 B2  Page 1 of 1
APPLICATION NO. : 10/849560
DATED : January 30, 2007
INVENTOR(S) : Nicoletta Almirante et al.

It is certified that error appears in the above-identified patent and that said Letters Patent is hereby corrected as shown below:

IN THE LETTERS PATENT:

Please amend the Letters Patent as follows:

Column 52, line 25, delete " 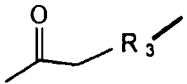 " and substitute therefor

-- 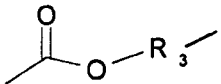 --;

Column 53, line 10, delete "Rf" and substitute therefor -- Rf' --;

Column 55, line 10, delete both occurrences "Rf" and substitute therefor -- Rf' --;

Column 60, line 34, delete "Q= —OCO—", and substitute therefor -- Q = —CO— --;

Column 65, line 35, delete both occurrences "Rf" and substitute therefor -- Rf' --.

Signed and Sealed this

Fourth Day of March, 2008

JON W. DUDAS
*Director of the United States Patent and Trademark Office*